US008968515B2

(12) United States Patent
Balan et al.

(10) Patent No.: US 8,968,515 B2
(45) Date of Patent: *Mar. 3, 2015

(54) METHODS FOR PRETREATING BIOMASS

(75) Inventors: Venkatesh Balan, East Lansing, MI (US); Bruce E. Dale, Mason, MI (US); Shishir Chundawat, East Lansing, MI (US); Leonardo Sousa, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/976,344

(22) Filed: Dec. 22, 2010

(65) Prior Publication Data
US 2011/0192559 A1    Aug. 11, 2011

Related U.S. Application Data

(63) Continuation-in-part of application No. 11/901,336, filed on Sep. 17, 2007, now Pat. No. 7,915,017, which is a continuation-in-part of application No. PCT/US2007/010415, filed on Apr. 30, 2007, application No. 12/976,344, which is a continuation of application No. PCT/US2010/035826, filed on May 21, 2010.

(60) Provisional application No. 60/796,375, filed on May 1, 2006, provisional application No. 61/180,308, filed on May 21, 2009.

(51) Int. Cl.
| | |
|---|---|
| D21C 11/00 | (2006.01) |
| D21C 9/10 | (2006.01) |
| D21C 3/22 | (2006.01) |
| C13K 1/02 | (2006.01) |
| B01J 3/00 | (2006.01) |
| C01C 1/00 | (2006.01) |
| C12P 19/14 | (2006.01) |
| C12P 7/10 | (2006.01) |
| C12P 19/02 | (2006.01) |
| C08B 1/00 | (2006.01) |

(52) U.S. Cl.
CPC . C12P 19/14 (2013.01); C12P 7/10 (2013.01); C12P 19/02 (2013.01); C08B 1/003 (2013.01); C12P 2201/00 (2013.01); Y02E 50/16 (2013.01)
USPC ........ 162/29; 162/63; 162/70; 127/2; 127/37; 423/352; 422/148

(58) Field of Classification Search
CPC .................................................. C12P 2201/00
USPC .......... 422/148; 435/100, 102, 105, 165, 277; 127/37
See application file for complete search history.

(56) References Cited

U.S. PATENT DOCUMENTS

| | | | |
|---|---|---|---|
| 2,017,779 | A | 10/1935 | Vosburgh |
| 2,548,192 | A | 4/1951 | Berg |
| 3,306,006 | A | 2/1967 | Urban |
| 3,920,419 | A | 11/1975 | Schroeder et al. |
| 4,064,276 | A | 12/1977 | Conradsen et al. |
| 4,153,435 | A | 5/1979 | Fischer |
| 4,263,744 | A | 4/1981 | Stoller |
| 4,287,162 | A | 9/1981 | Scheibel |
| 4,356,196 | A | 10/1982 | Hultquist |
| 4,370,351 | A | 1/1983 | Harper |
| 4,461,648 | A * | 7/1984 | Foody ............................ 127/37 |
| 4,526,791 | A | 7/1985 | Young |
| 4,581,044 | A | 4/1986 | Uno et al. |
| 4,589,334 | A | 5/1986 | Andersen |
| 4,594,131 | A | 6/1986 | Maier |
| 4,600,590 | A | 7/1986 | Dale |
| 4,624,805 | A | 11/1986 | Lawhon |
| 4,644,060 | A | 2/1987 | Chou |
| 4,848,026 | A | 7/1989 | Dunn-Coleman |
| 4,986,835 | A | 1/1991 | Uno et al. |
| 4,995,888 | A | 2/1991 | Beaupre et al. |
| 5,025,635 | A | 6/1991 | Rockenfeller et al. |
| 5,037,663 | A | 8/1991 | Dale |
| 5,047,332 | A | 9/1991 | Chahal |
| 5,114,694 | A | 5/1992 | Grotz, Jr. |
| 5,171,592 | A * | 12/1992 | Holtzapple et al. ............. 426/69 |
| 5,370,999 | A | 12/1994 | Stuart |
| 5,473,061 | A | 12/1995 | Bredereck et al. |
| 5,660,603 | A | 8/1997 | Elliot et al. |
| 5,736,032 | A | 4/1998 | Cox et al. |
| 5,865,898 | A | 2/1999 | Holtzapple et al. |
| 5,939,544 | A | 8/1999 | Karstens et al. |
| 6,027,552 | A | 2/2000 | Ruck et al. |

(Continued)

FOREIGN PATENT DOCUMENTS

| | | |
|---|---|---|
| AU | 756976 B2 | 1/2003 |
| CA | 2368872 A1 | 10/2000 |

(Continued)

OTHER PUBLICATIONS

Zhu J-X et al. Concurrent Downflow Circulating Fluidized Bed (Downer) Reactors-A State of the Art Review, Can J Chem Eng 73: 662-677, 1995.*

(Continued)

Primary Examiner — Taeyoon Kim
Assistant Examiner — Srikanth Patury
(74) Attorney, Agent, or Firm — Clark IP Law, PLC

(57) ABSTRACT

A method of alkaline pretreatment of biomass, in particular, pretreating biomass with gaseous ammonia.

30 Claims, 12 Drawing Sheets

(56) References Cited

U.S. PATENT DOCUMENTS

| | | | |
|---|---|---|---|
| 6,106,888 | A | 8/2000 | Dale et al. |
| 6,176,176 | B1 | 1/2001 | Dale et al. |
| 6,255,505 | B1 | 7/2001 | Bijl et al. |
| 6,416,621 | B1 | 7/2002 | Karstens |
| 6,425,939 | B1 | 7/2002 | Moreau et al. |
| 6,444,437 | B1 | 9/2002 | Sporleder et al. |
| 6,524,848 | B2 | 2/2003 | McNelly |
| 6,585,807 | B2 | 7/2003 | Umino et al. |
| 6,620,292 | B2 * | 9/2003 | Wingerson ............. 162/19 |
| 6,872,296 | B2 | 3/2005 | Kim |
| 6,893,484 | B2 | 5/2005 | Thomas |
| 7,049,485 | B2 | 5/2006 | Sticklen et al. |
| 7,187,176 | B2 | 3/2007 | Lim et al. |
| 7,250,074 | B2 | 7/2007 | Tonkovich et al. |
| 7,371,926 | B2 | 5/2008 | Sticklen |
| 7,371,962 | B2 | 5/2008 | Zuppero et al. |
| 7,494,675 | B2 | 2/2009 | Abbas et al. |
| 7,494,792 | B2 | 2/2009 | Warzywoda et al. |
| 7,537,744 | B2 | 5/2009 | Benderly et al. |
| 7,585,652 | B2 | 9/2009 | Foody et al. |
| 7,771,565 | B2 | 8/2010 | Kirov et al. |
| 7,910,338 | B2 | 3/2011 | Hennessey et al. |
| 7,910,675 | B2 | 3/2011 | Funk et al. |
| 7,915,017 | B2 | 3/2011 | Dale |
| 7,937,851 | B2 | 5/2011 | Rajagopalan et al. |
| 8,020,342 | B2 | 9/2011 | Karpik |
| 8,030,030 | B2 | 10/2011 | Varanasi et al. |
| 8,367,378 | B2 | 2/2013 | Balan et al. |
| 8,394,177 | B2 | 3/2013 | Campbell et al. |
| 8,394,611 | B2 | 3/2013 | Dale et al. |
| 8,419,900 | B2 | 4/2013 | Baba et al. |
| 8,444,925 | B2 | 5/2013 | Baba |
| 8,551,549 | B2 | 10/2013 | Zeeck |
| 8,651,403 | B2 | 2/2014 | Camp et al. |
| 8,673,031 | B2 | 3/2014 | Dale et al. |
| 8,771,425 | B2 | 7/2014 | Dale |
| 8,846,123 | B2 | 9/2014 | Zeeck |
| 2003/0044951 | A1 | 3/2003 | Sporleder et al. |
| 2005/0064577 | A1 | 3/2005 | Berzin |
| 2005/0233423 | A1 | 10/2005 | Berka et al. |
| 2006/0014260 | A1 | 1/2006 | Fan et al. |
| 2006/0130396 | A1 | 6/2006 | Werner |
| 2006/0177917 | A1 | 8/2006 | Warzywoda et al. |
| 2007/0029252 | A1 * | 2/2007 | Dunson et al. ............. 210/603 |
| 2007/0031918 | A1 * | 2/2007 | Dunson et al. ............. 435/41 |
| 2007/0037259 | A1 | 2/2007 | Hennessey et al. |
| 2007/0113736 | A1 | 5/2007 | Bandosz |
| 2007/0192900 | A1 | 8/2007 | Sticklen |
| 2007/0202214 | A1 | 8/2007 | Lewis et al. |
| 2007/0227063 | A1 | 10/2007 | Dale et al. |
| 2007/0287795 | A1 | 12/2007 | Huda et al. |
| 2008/0008783 | A1 | 1/2008 | Dale |
| 2008/0057555 | A1 | 3/2008 | Nguyen |
| 2008/0087165 | A1 | 4/2008 | Wright et al. |
| 2008/0115415 | A1 | 5/2008 | Agrawal et al. |
| 2008/0171297 | A1 | 7/2008 | Reynolds et al. |
| 2008/0229657 | A1 | 9/2008 | Senyk et al. |
| 2008/0256851 | A1 | 10/2008 | Lumb |
| 2008/0264254 | A1 | 10/2008 | Song et al. |
| 2008/0280236 | A1 | 11/2008 | Wright |
| 2009/0011474 | A1 | 1/2009 | Balan et al. |
| 2009/0042259 | A1 | 2/2009 | Dale et al. |
| 2009/0049748 | A1 | 2/2009 | Day et al. |
| 2009/0053770 | A1 | 2/2009 | Hennessey et al. |
| 2009/0053771 | A1 | 2/2009 | Dale et al. |
| 2009/0061486 | A1 | 3/2009 | Edwards et al. |
| 2009/0087898 | A1 | 4/2009 | Haase et al. |
| 2009/0093027 | A1 | 4/2009 | Balan et al. |
| 2009/0099079 | A1 | 4/2009 | Emalfarb et al. |
| 2009/0123361 | A1 | 5/2009 | Johannessen et al. |
| 2009/0178671 | A1 | 7/2009 | Ahring |
| 2009/0221042 | A1 | 9/2009 | Dale et al. |
| 2009/0230040 | A1 | 9/2009 | Limcaco |
| 2009/0313976 | A1 | 12/2009 | Johannessen et al. |
| 2009/0318670 | A1 | 12/2009 | Dale et al. |
| 2010/0159521 | A1 | 6/2010 | Cirakovic et al. |
| 2010/0267999 | A1 | 10/2010 | Lau et al. |
| 2010/0279361 | A1 | 11/2010 | South et al. |
| 2011/0192559 | A1 | 8/2011 | Venkatesh |
| 2011/0201091 | A1 | 8/2011 | Dale |
| 2011/0290114 | A1 | 12/2011 | Campbell et al. |
| 2011/0300269 | A1 | 12/2011 | Dale et al. |
| 2012/0064574 | A1 | 3/2012 | Tokuyasu et al. |
| 2012/0071308 | A1 | 3/2012 | Sekar |
| 2012/0085505 | A1 | 4/2012 | Sabourin |
| 2012/0125548 | A1 | 5/2012 | Cohen |
| 2012/0125551 | A1 | 5/2012 | Cohen et al. |
| 2012/0187228 | A1 | 7/2012 | Camp et al. |
| 2012/0325202 | A1 | 12/2012 | Dale et al. |
| 2013/0196398 | A1 | 8/2013 | Bals et al. |
| 2013/0217073 | A1 | 8/2013 | Chundawat et al. |
| 2013/0247456 | A1 | 9/2013 | Dale et al. |
| 2013/0280762 | A1 | 10/2013 | Dale et al. |
| 2013/0289268 | A1 | 10/2013 | Teymouri et al. |
| 2014/0038243 | A1 | 2/2014 | Balan et al. |
| 2014/0227757 | A1 | 8/2014 | Jin et al. |

FOREIGN PATENT DOCUMENTS

| | | | |
|---|---|---|---|
| CA | 2573046 A1 | 1/2006 | |
| CA | 2610797 A1 | 12/2006 | |
| CA | 2752604 A1 | 8/2010 | |
| CA | 2762985 | 7/2013 | |
| CA | 2650860 C | 9/2013 | |
| CA | 2737704 C | 11/2013 | |
| CN | 20060177917 A1 | 8/2006 | |
| CN | 101223273 A | 7/2008 | |
| CN | 20090318670 A1 | 12/2009 | |
| CN | 102597247 A | 7/2012 | |
| CN | 102939388 A | 2/2013 | |
| DE | 20301645 | 4/2003 | |
| EP | 0144930 A2 * | 6/1985 | ............ A23K 1/12 |
| EP | 1247781 A2 | 10/2002 | |
| EP | 1533279 A1 | 5/2005 | |
| EP | 1690944 A1 | 8/2006 | |
| GB | 1310835 | 3/1973 | |
| GB | 1381728 A | 1/1975 | |
| GB | 2122864 A | 1/1984 | |
| IN | 249187 | 10/2011 | |
| IN | 9645/DELNP/2011 A | 2/2013 | |
| JP | 2008161125 A | 7/2008 | |
| JP | 2008-535664 A | 9/2008 | |
| JP | 2011160753 A | 8/2011 | |
| RU | 22157655 C1 | 11/2003 | |
| WO | 8500133 | 1/1985 | |
| WO | WO-8500133 A1 | 1/1985 | |
| WO | 00/61858 A1 | 10/2000 | |
| WO | 01/32715 A1 | 5/2001 | |
| WO | WO-0237981 A2 | 5/2002 | |
| WO | 2004/033920 A1 | 4/2004 | |
| WO | 2005/091418 A2 | 9/2005 | |
| WO | 2006/055362 A1 | 5/2006 | |
| WO | 2006128304 A1 | 12/2006 | |
| WO | WO-2007005918 A2 | 1/2007 | |
| WO | WO-2007005918 A3 | 1/2007 | |
| WO | WO 2007130337 A1 * | 11/2007 | |
| WO | WO-2007130337 A1 | 11/2007 | |
| WO | WO-2008020901 A2 | 2/2008 | |
| WO | 2008/020901 A3 | 7/2008 | |
| WO | 2008/114139 A2 | 9/2008 | |
| WO | 2008/114139 A3 | 12/2008 | |
| WO | 2009/045527 A1 | 4/2009 | |
| WO | WO-2010098408 A1 | 9/2010 | |
| WO | 2010/121348 A1 | 10/2010 | |
| WO | WO-2010135679 A1 | 11/2010 | |
| WO | 2010147218 A1 | 12/2010 | |
| WO | WO-2010147218 A1 | 12/2010 | |
| WO | WO-2011028543 A2 | 3/2011 | |
| WO | 2011/046818 A2 | 4/2011 | |
| WO | 2011/028543 A3 | 6/2011 | |
| WO | 2011/080154 A1 | 7/2011 | |
| WO | 2011/125056 A1 | 10/2011 | |
| WO | 2011/133571 A2 | 10/2011 | |
| WO | 2011133571 A3 | 10/2011 | |

(56) References Cited

FOREIGN PATENT DOCUMENTS

| WO | WO-2012012594 A1 | 1/2012 |
|---|---|---|
| WO | 2012071312 A2 | 5/2012 |
| WO | WO-2012088429 A2 | 6/2012 |
| WO | 2013106113 A2 | 7/2013 |
| WO | 2013131015 A1 | 9/2013 |
| WO | 2013/106113 A3 | 10/2013 |

OTHER PUBLICATIONS

Anhydrous Ammonia, Customer Manual, Dec. 2006.*
"U.S. Appl. No. 11/901,336, Response filed Mar. 29, 2010 to Restriction Requirement mailed Mar. 11, 2010", 9 pgs.
"U.S. Appl. No. 11/901,336, Non Final Office Action mailed Apr. 27, 2010", 10 pgs.
"U.S. Appl. No. 11/901,336, Notice of Allowance mailed Aug. 24, 2010", 5 pgs.
"U.S. Appl. No. 11/901,336, Response filed Jul. 28, 2010 to Non Final Office Action mailed Apr. 27, 2010", 11 pgs.
"U.S. Appl. No. 11/901,336, Restriction Requirement mailed Mar. 11, 2010", 9 pgs.
"U.S. Appl. No. 12/226,763, Preliminary Amendment filed Dec. 16, 2008", 4 pgs.
"U.S. Appl. No. 12/976,344, Preliminary Amendment filed Apr. 27, 2011", 10 pgs.
"Australian Application Serial No. 2007248736, Australian Office Action mailed Dec. 1, 2009", 2 pgs.
"Australian Application Serial No. 2007248736, Response filed Mar. 24, 2010 to Australian Office Action mailed Dec. 1, 2009", 7 pgs.
"Canadian Application Serial No. 11/901,336, Response filed Jun. 29, 2011 to Office Action mailed May 12, 2011", 2 pgs.
"Canadian Application Serial No. 2,650,860, Office Action mailed May 12, 2011", 2 pgs.
"European Application Serial No. 07776479.3, Amendment (new claims) dated Dec. 16, 2010", 9 pgs.
"European Application Serial No. 07776479.3, Extended European Search Report mailed May 26, 2010", 6 pgs.
"Indian Application Serial No. 5933/CHENP/2008, Office Action mailed Oct. 29, 2010", English translation, 2 pgs.
"International Application Serial No. PCT/US2007/10415, International Search Report mailed Oct. 11, 2007", 2 pgs.
"International Application Serial No. PCT/US2007/10415, Written Opinion mailed Sep. 17, 2007", 4 pgs.
"International Application Serial No. PCT/US2010/035826, International Search Report mailed Jul. 13, 2010", 2 pgs.
Alizadeh, Hasan, et al., "Pretreatment of Switchgrass by Ammonia Fiber Explosion", Applied Biochemistry and Biotechnology 121-124, (2005), 1133-1141.
Chundawat, Shishir Pratap Singh, "Ultrastructural and physicochemical modifications within ammonia treated lignocellulosic cell walls and their influence on enzymatic digestibility", Ph.D., Michigan State University, (2010), 469 pgs.
Eggeman, Tim I, et al., "Process and Economic Anaylsis of Pretreatment Technologies", Bioresource Technology, 96, (2005), 2019-2025.
Felix, A., et al., "In Vitro and In Vivo Digestibility of Soya-Bean Straw Treated with Various Alkalis", Anim. Prod, 51, (1990), 47-61.
Kudra, T., et al., "Superheating Steam Drying", Advanced Drying Technologies, New York, NY : Marcel Dekker, Inc., (2002), 81-111.
Mosier, Nathan, et al., "Features of promising technologies for pretreatment of lignocellulosic biomass", Bioresour Technol., 96(6), (Apr. 2005), 673-86.
Teymouri, F., et al., "Optimization of the ammonia fiber explosion (AFEX) treatment parameters for enzymatic hydrolysis of corn stover", Bioresour Technol., 96(18), (Dec. 2005), 2014-18.
Waiss, Jr, A. C, et al., "Improving Digestibility of Straws for Ruminant Feed by Aqueous Ammonia", Journal of Animal Science; 35(1), (1972), 109-112.
U.S. Appl. No. 11/729,632, Response filed Sep. 11, 2009 to Non Final Office Action mailed May 6, 2009, 9 pgs.
Ferrer, Sulbaran B., "Sugar Production from Rice Straw", Suppl. 1, Arch Latinoam Prod Anim 5, (1997),112-114.
U.S. Appl. No. 12/286,913, Response filed Dec. 28, 2011 to Non Final Office Action mailed Sep. 28, 2011, 13 pgs.
Mosier, Nathan "Features of Promising Technologies for Pretreatment of Lignocellulosic Biomass", Bioresource Technology, vol. 96, No. 6, (Apr. 2005),673-686.
International Application Serial No. PCT/US2010/046525, Search Report mailed Apr. 29, 2011, 5 pgs.
European Application Serial No. 11162906.9, Office Action mailed Jan. 16, 2012, 2 pgs.
Miller, Norman "Re: Commitment Letter "Phase I Biomass Enhanced Refined Lignite Demonstration Project"", http://www.nd.gov/ndic/renew/meeting0903/r005-a-prop.pdf, (Dec. 2008), 24 pgs.
International Application Serial No. PCT/US2011/066868, PCT Search Report (3 pgs.), mailed Sep. 19, 2012.
U.S. Appl. No. 11/729,632, Examiner Interview Summary filed Oct. 30, 2009, 9 pgs.
U.S. Appl. No. 11/729,632, Non Final Office Action mailed May 6, 2009, 4 pgs.
U.S. Appl. No. 11/729.632, Response filed Sep. 11, 2009 to Non Final Office Action mailed May 6, 2009, 9 pgs.
U.S. Appl. No. 12/229,225, Non Final Office Action mailed Aug. 16, 2011, 6 pgs.
U.S. Appl. No. 12/229,225 Response filed Nov. 15, 2011 to Non Final Office Action mailed Aug. 16, 2011, 12 pgs.
Chahal, D. S., "Bioconversion of Hemicelluloses into Useful Products in an Intergrated Process for Food/Feed and Fuel (Ethanol) Production from Biomass", Hemicellulose Bioconversion, Biotechnol, Bioeng. Symp., (1984), 425-433.
Chang, Shu-Ting "The World Mushroom Industry: Trends and Technological Development", International Journal of Medicinal Mushrooms, (2006), 297-314.
Ferrer, Sulbaran B., "Sugar Production from Rice Straw", Suppl, 1, Arch Latinoam Prod Anim 5, (1997), 112-114.
U.S. Appl. No. 12/286,913, Response filed Dec. 28, 2011 to Non Final Office Action mailed Sep. 28, 2011. 13 pgs.
U.S. Appl. No. 12/226,763, Response filed Dec. 21, 2011 to Non Final Office Action mailed Aug. 22, 2011, 11 pgs.
U.S. Appl. No. 12/226,763, Final Office Action mailed Jan. 10, 2012, 16 pgs.
Lin, K et al., "Chemical Engineer's Handbook", 5. sup. th Edition 1973 Chapter 4 McGraw-Hill N.Y, (1973).
Canadian Application Serial No. 2,650,860, Office Action mailed Oct. 24, 2011, 3 pgs.
Indian Application Serial No. 5933/CHENP/2008, Response filed Sep. 14, 2011 to Office Action mailed Oct. 14, 2010, 11 pgs.
Mosier, Nathan "Features of Promising Technologies for Pretreatment of Lignocellulosic Biomass", Bioresource Technology, vol. 96, No. 6, (Apr. 2005), 673-686.
International Application Serial No. PCT/US2007/010415, International Search Report mailed Oct. 11, 2007, 2 pgs.
International Application Serial No. PCT/US2007/010415, Written Opinion mailed Oct. 11, 2007, 4 pgs.
U.S. Appl. No. 12/226,763, Non Final Office Action mailed Aug. 22, 2011, 13 pgs.
International Application Serial No. PCTIUS2010/046525, Search Report mailed Apr. 29, 2011, 5 pgs.
International Application Serial No. PCT/US2010/046525, Written Opinion mailed Apr. 29, 2011, 4 pgs.
U.S. Appl. No. 11/897,119, Restriction Requirement mailed Sep. 30, 2011, 6 pgs.
U.S. Appl. No. 12/229,225, Final Office Action Mailed Jan. 6, 2012, 7 pgs.
U.S. Appl. No. 11/729,632, Notice of Allowance mailed Nov. 16, 2009, 7 pgs.
U.S. Appl. No. 12/229,225, Response filed Nov. 15, 2011 to Non Final Office Action mailed Aug. 16, 2011, 12 pgs.
U.S. Appl. No. 12/286,913, Non Final Office Action mailed Mar. 1, 2012, 7 pgs.
European Application Serial No. 10778488.6, Office Action mailed Dec. 30, 2011, 2 pgs.

(56) References Cited

OTHER PUBLICATIONS

European Application Serial No. 11162906.9, Office Action mailed Jan. 16, 2012.
Chinese Application Serial No. 200780025394.4, Office Action mailed Oct. 13, 2011, (with English translation), 11 pgs.
Adaoa, P. et al., "Compression Characteristics of Selected Ground Agricultural Biomass", Agricultural Engineering International: The CIGR Ejournal, Manuscript 1347, vol. XI, (Jun. 2009), 19 pgs.
Kaliyan, N. et al., "Roll Press Briquetting and Pelleting of Corn Stover and Switchgrass", Transactions of the ASABE, vol. 52, No. 2, (2009), 543-555.
Miller, Norman "Re: Commitment Letter Phase I Biomass Enhanced Refined Lignite Demonstration Project", http://www.nd.gov/ndic/renew/meeting0903/r005-a-prop.pdf, (Dec. 2008), 24 pgs.
Teymouri, Farzaneh et al., "Optimization of the Ammonia Fiber Explosion (AFEX) Treatment Parameters for Enzymatic Hydrolysis of Corn Stover", Bioresource Tech, vol. 96, No. 18, (2005), 2014-2018.
Canadian Application Serial No. 2,650,860, Response filed Apr. 23, 2012 to Office Action mailed Nov. 14, 2011, 10 pgs.
Candian Application Serial No. 2,760,840, Office Action mailed Mar. 28, 2012, 3 pgs.
U.S. Appl. No. 12/226,763, Response filed May 10, 2012 to Office Action mailed Dec. 21, 2011 (14 pgs.).
U.S. Appl. No. 12/226,763, Notice of Allowance Mailed Oct. 1, 2012.
U.S. Appl. No. 12/286,913, Notice of Allowance Mailed Oct. 3, 2012.
U.S. Appl. No. 12/763,102, Response Filed Oct. 17, 2012 to Office Action Mailed Sep. 17, 2012.
U.S. Appl. No. 12/791,703, Response Filed Oct. 11, 2012 to Office Action Mailed Jul. 27, 2012.
U.S. Appl. No. 13/202,011, Office Action Mailed Sep. 27, 2012.
U.S. Appl. No. 13/591,092, Office Action Mailed Dec. 13, 2012.
Australian Application No. 2010289797, Examination Report Mailed Oct. 30, 2012.
Australian Application No. 2012249409, Examination Report Mailed Aug. 30, 2012.
Canadian Application No. 2,650,860, Response Filed Dec. 13, 2012 to Office Action Mailed Jun. 18, 2012.
Canadian Application No. 2,737,704, Office Action Mailed on Nov. 5, 2012.
Canadian Application No. 2,760,840, Response Filed Nov. 6, 2012 to Office Action Mailed Aug. 6, 2012.
Canadian Application No. 2,762,985, Response Filed Oct. 5, 2012 to Office Action Mailed Jul. 6, 2012.
Chinese Application No. 200780025394.4 Office Action Mailed Oct. 30, 2012.
European Application No. 07776479.6, Response Filed Sep. 30, 2012 to Office Action Mailed May 30, 2012.
European Application No. 07776479.3, Office Action Mailed Dec. 5, 2012.
European Application No. 11772569.7, Office Action Mailed Nov. 30, 2012.
International Application No. PCT/US2011/066868, Written Opinion Mailed Sep. 19, 2012.
Bergner, Hans, "Archives of Animal Nutrition", Arch. Tierenahr., vol. 30, 1980, 19pgs.
Deshusses, Marc A., "Biological Waste Air Treatment in Biofilters", Current Opinion in Biotechnology, vol. 8, 1997, 335-339.
Sheridan, B.A. et al., "Assessment of the Influence of Media Particle Size on the Biofiltration of Odorous Exhaust Ventilation Air from a Piggery Faciliyt", Bioresource Technology, vol. 84, 2002, 129-143.
Zhang, Xianglan et al., "The Effect of Different Treatment Conditions on Biomass Binder Preparation For Lignite Briquette", Fuel Processing Technology, vol. 73, 2001, 185-196.
Canadian Application Serial No. 2,760,840, Office Action mailed Mar. 28, 2012, 3 pgs.
U.S. Appl.No. 12/226,763, Notice of Allowance mailed May 29, 2012, 9 pgs.
European Application Serial No. 07776479.3, Communication pursuant to Article 94(3) EPC, mailed May 30, 2012, 6 pgs.
U.S. Appl. No. 12/763,102, Restriction Requirement mailed Sep. 17, 2012, 11 pgs.
Mexico Application Serial No. MX/a/2011/012357, Office Action mailed Aug. 21, 2012, 1 pgs.
Chinese Application Serial No. 200680023897.3. Chinese Office Action mailed Jun. 30, 2006.
Chinese Application No. 20108022215.3, Chinese Notice of Publication No. dated Jul. 18, 2012.
Australian Application Serial No. 2011201768, Examiner Report mailed Jun. 21, 2012, 3 pgs.
Canadian Application Serial No. 2,762,985, Office Action mailed Mar. 13, 2012, 4 pgs.
Canadian Application Serial No. 2,737,704, Office Action mailed Jun. 4, 2012, 4 pgs.
Canadian Application U.S. Appl. No. 2,650,860, Office Action mailed Jun. 18, 2012, 2 pgs.
Canadian Application Serial No. 2,762,986, Office Action mailed Jul. 6, 2012, 2 pgs.
Canadian Application Serial No. 2,760,840, Office Action mailed Aug. 6, 2012, 4 pgs.
Canadian Application Serial No. 2,760,840, Response filed Jun. 27, 2012 to Office Action mailed Mar. 28, 2012, 5 pgs.
Canadian Application Serial No. 2,762,985, Response filed Jun. 12, 2012 to Office Action mailed Mar. 13, 2012, 7 pgs.
Canadian Application Serial No. 2,737,704, Response filed Aug. 22, 2012 to Office Action mailed Jun. 4, 2012, 26 pgs.
Chinese Application Serial No. 201110097994.X, Office Action mailed Jul. 30, 2012, 25 pgs.
European Application Serial No. 11162906.9, Response filed Jul. 5, 2012 to Office Action mailed Jan. 16, 2012, 10 pgs.
Cen, Peilin et al., "Production of Cellulase by Solid-State Fermentation", Advances in Biochecmical Engineering/Biotechnology, vol. 65, (Jan. 1, 1990), 70-92.
Chahal, Parmimder atal., "Production of Cellulase in Solid-State Fermentation with Trichoderma Reesai MCG 80 on Wheat Straw", Applied Biochemistry and Biotechnology, vol. 57-58, No. 1, (1996), 433-442.
Chinedu Nwodo, S. et al., "Xylanase Production of Aspergillus Niger and Penicillium Chrysogenum from Ammonia Pretreated Cellulosic Waste", Research Journal of Microbiology, vol. 3, No. 4, (2008), 246-253.
Jain, Arpan et al., "Effect of Ammonia Pretreatment on Switchgrass for Production of Cellulase using Trichoderma Reesai Rut C-30", Symposium Onbiotechnology for Fuels and Chemicals, Poster Session 2, abstract, Accessed Aug. 11, 2011 <http://sim.confex.com/sim/31st/techprogram/P8269.HTM>, (May 4, 2009), 1 pg.
Kumar, Parveen et al., "Methods for Pretreatment of Lignocellulosic Biomass for Efficient Hydrolysis and Biofuel Production", Ind. Eng. Chem. Res., vol. 48, No. 8, (Mar. 20, 2009), 3713-3729.
Lynd, Lee R., et al., "Microbial Cellulose Utilization: Fundamentals and Biotechnology", Microbiology and Molecular Biology Reviews, vol. 66, No. 3, (Sep. 2002), 506-577.
Mangold, Ernst "Archives of Animal Nutrition", Arch. Tierernahr,, vol. 30, (1980), 1-12, 1-864.
Perry, John H., "Reactor Design", Chemical Engineers' Handbook, 4th Edition, (1969), Apr. 21-Apr. 24.
Singhania, Reeta R., et al., "Advancement and Comparative Profiles in the Production Technologies using Solid-State and Submerged Fermentation for Microbial Cellulases", Enzyme and Microbial Technology, vol. 46, No. 7, (Jun. 7, 2010), 541-549.
Warzywoda, Michel et al., "Production and Characterization of Cellulolytic Enzymes from Trichoderma Reesei Grown on Various Carbon Sources", Bioresource Technology, vol. 39, No. 2, (1992), 125-130.
International Application Serial No. PCT/US2010/046525, Preliminary Report on Patentability mailed Mar. 8, 2012, 6 pgs.
Chinese Application No. 201110097994X Response filed Jul. 11, 2013 to Office Action mailed on Mar. 27, 2013.
Chinese Application No. 201210287568.7 Office Action mailed on Jul. 26, 2013.
European Application No. 10814256.3 EPC Article 94 (3) mailed on Sep. 6, 2013.

(56) References Cited

OTHER PUBLICATIONS

European Application No. 10814256.3 Response filed Aug. 7, 2013 for Office Action mailed Feb. 11, 2013.
European Application No. 11162906.9 Response filed Jul. 7, 2013 for Office Action mailed Mar. 6, 2013.
International Application No. PCT/US2011/066868 PCT Notice of Transmittal of IPRP mailed on Jul. 4, 2013.
International Application No. PCT/US2012/059898 PCT Notice of Transmittal of Int'l Search Report mailed on Jul. 26, 2013.
Wilson, Jonathan, "A Cost Analysis for the Densification and Transportation of Cellulosic Biomass for Ethanol Production", Kansas State University, 2009, 86 pgs.
Topic 3 R&D on Processes for Solid, Liquid and Gaseous Fuels From Biomass, Jun. 22, 2012 20th EU BC&E.
Zhu, J.-X. et al. Cocurrent downflow circulating fluidized bed (downer) reactors—A state of the art review, Can J Chem Eng 73: 662-677, Oct. 1, 1995.
U.S. Appl. No. 12/226,763, Notice of Allowance Mailed on Jan. 22, 2013.
U.S. Appl. No. 12/763,102 Office Action Mailed Dec. 24, 2012.
U.S. Appl. No. 12/763,102 Response Filed Mar. 25, 2013 to Office Action Mailed Dec. 24, 2012.
U.S. Appl. No. 13/202,011, Response Filed Dec. 21, 2012 to Office Action Mailed Sep. 27, 2012 on Jan. 22, 2013.
U.S. Appl. No. 13/202,011 Supplemental Response filed Feb. 25, 2013 to Office Action Mailed Sep. 27, 2012.
U.S. Appl. No. 13/202,011, Second Supplemental Response filed Mar. 21, 2013 to Office Action Mailed Sep. 27, 2012.
U.S. Appl. No. 13/202,011 Notice of Allowance mailed on Apr. 9, 2013.
U.S. Appl. No. 13/202,011 Request for Continued Examination filed Jul. 3, 2013.
U.S. Appl. No. 13/458,830 Preliminary Amendment filed Apr. 12, 2013.
U.S. Appl. No. 13/591,092, Response Filed Mar. 13, 2013 to Office Action Mailed Dec. 13, 2012.
U.S. Appl. No. 13/591,092, Final Office Action Mailed Mar. 25, 2013.
U.S. Appl. No. 13/591,092 Response to Provoke filed May 23, 2013.
U.S. Appl. No. 13/591,092 Advisory Action mailed Jun. 6, 2013.
U.S. Appl. No. 13/591,092 Request for Continued Examination with Amendment filed Jun. 25, 2013.
U.S. Appl. No. 13/997,043 Preliminary Amendment filed on Jun. 21, 2013.
Australian Application No. 2013205685 Supplemental Amendment filed Jun. 3, 2013.
Brazilian Application No. PI0722418-4, Office Action Jan. 14, 2013.
Canadian Application No. 2,650,860 Notice of Allowance mailed on Apr. 2, 2013.
Canadian Application No. 2,650,860 Amendment after Allowance filed May 27, 2013.
Canadian Application No. 2,650,860 Amendment after Allowance filed Jun. 13, 2013.
Canadian Application No. 2,737,704, Response Filed Jan. 30, 2013 to Office Action Mailed on Nov. 5, 2012.
Canadian Application No. 2,737,704, Office Action Mailed on Feb. 21, 2013.
Canadian Application No. 2,737,704, Response Filed May 21, 2013 to Office Action Mailed on Feb. 21, 2013.
Canadian Application No. 2,760,840, Office Action Mailed on Jan. 3, 2013.
Canadian Application No. 2,760,840 Response filed Mar. 28, 2013 to Office Action mailed on Jan. 3, 2013.
Canadian Application No. 2,760,840 Supplemental Amendment filed May 16, 2013.
Chinese Application No. 200780025394.4, Response Filed Jan. 14, 2013 to Office Action Mailed Oct. 30, 2012.
Chinese Application No. 200780025394.4 Office Action mailed Mar. 27, 2013.
Chinese Application No. 200780025394.4, Response Filed Jun. 11, 2013 to Office Action Mailed Mar. 27, 2013.
Chinese Application No. 201110097994.X, Response Filed Jan. 14, 2013 to Office Action Mailed on Jul. 30, 2012.
Chinese Application No. 201110097994X Office Action mailed on Mar. 27, 2013.
European Application No. 07776479.3 Response filed Apr. 5, 2013 to Office Action mailed Dec. 5, 2012.
European Application No. 07776479.3 EPC Rule 115(1) Summons to Oral Proceedings mailed on May 7, 2013.
European Application No. 10814256.3, Search Report Mailed on Jan. 23, 2013.
European Application No. 11162906.9, EPC Article 94(3) Mailed on Mar. 6, 2013.
Indian Application No. 110/DELNP/2012 Supplemental Amendment filed May 14, 2013.
International Application No. PCT/US2013/028689 International Search Report and Written Opinion mailed on Jun. 4, 2013.
Carolan, Joseph E. et al., "Technical and Financial Feasibility Analysis of Distributed Bioprocessing Using Regional Biomass Pre-Processing Centers", Journal of Agricultural & Food Industrial Organization, vol. 5 Issue 2, 2007, 29 pgs.
Compakco, LLC et al., "Phase I Biomass Enhanced Refined Lignite Demonstration Project", Dec. 15, 2008, 24pgs.
"Marshall" Complete Rations for Dairy Cattle. II. Sugarcane Bagasse Pellets as Roughage in Blended Rations for Lactating Cows.
"Roman" Complete Rations for Dairy Cattle. V. Interaction of Sugarcane Bagasse Quantity and Form with Soybean Meal, Urea, and Starea.
U.S. Appl. No. 12/763,102 Final Office Action mailed on Aug. 5, 2013.
U.S. Appl. No. 13/202,011 Request for Continued Examination filed on Jul. 3, 2013.
U.S. Appl. No. 13/886,021 Preliminary Amendment filed Jul. 25, 2013.
Australian Application No. 2010249409 Amendment filed Aug. 28, 2013.
Australian Application No. 2010249409 Response filed Aug. 27, 2013 to Examination Report mailed on Aug. 30, 2012.
Australian Application No. 2011201768 Response filed Aug. 2, 2013 to Examination Report mailed on Jun. 21, 2012.
Canadian Application No. 2737704 Supplemental Amendment filed Jul. 30, 2013.
Canadian Application No. 2760840 Non-Final Office Action mailed on Jul. 30, 2013.
Chinese Application No. 200780025394.4 Office Action mailed on Jul. 26, 2013.
Final Office Action received for U.S. Appl. No. 12/229,225, mailed on Jan. 6, 2012, 7 pages.
Notice of Allowance received for U.S. Appl. No. 12/226,763, mailed on May 29, 2012, 9 pages.
Advisory Action received for U.S. Appl. No. 12/763,102, mailed on Dec. 6, 2013, 3 pages.
Office Action received for Brazilian Patent Application No. 0722418-4, mailed on Jan. 14, 2013. 3 pages.
Extended European Search Report received for European Patent Application No. 07776479.3. mailed on May 26, 2010, 6 pages.
Office Action received for European Patent Application No. 10814256.3, mailed on Sep. 6. 2013, 4 pages.
Extended European Search Report received for European Patent Application No. 10814256.3. mailed on Jan. 23, 2013, 6 pages.
Non Final Office Action received for U.S. Appl. No. 11/729,632, mailed on May 6. 2009, 5 pages.
Extended European Search Report received for European Patent Application No. 11162906.9, mailed on Dec. 13, 2011, 14 pages.
Office Action received for European Patent Application No. 11162906.9, mailed on Mar. 6, 2013, 5 pages.
Partial European Search Report received for EP Patent Application No. 11162906.9. mailed on Aug. 23. 2011, 9 pages.
Extended European Search Report for European Patent Application No. 11850707.8. mailed on Jul. 3, 2014, 8 pages.
Non Final Office Action received for U.S. Appl. No. 12/214,687, mailed on Jun. 2, 2011, 5 pages.
Notice of Allowance received for U.S. Appl. No. 12/226,763, mailed on Jan. 22. 2013, 7 pages.

(56) References Cited

OTHER PUBLICATIONS

Restriction Requirement received for U.S. Appl. No. 12/226,850, mailed on Jun. 30. 2011, 4 pages.
Non Final Office Action received for U.S. Appl. No. 12/286,913, mailed on Sep. 28, 2011, 7 pages.
Final Office Action received for U.S. Appl. No. 12/763,102, mailed on Aug. 5, 2013. 12 pages.
Non Final Office Action received for U.S. Appl. No. 12/763,102, mailed on Dec. 24, 2012, 8 pages.
Restriction Requirement received for U.S. Appl. No. 13/202,011, mailed on Jul. 17. 2012, 6 pages.
Notice of Allowance received for U.S. Appl. No. 13/202,011, mailed on Apr. 9, 2013, 9 pages.
Notice of Allowance received for U.S. Appl. No. 13/202,011, mailed on Nov. 8. 2013, 7 pages.
Notice of Allowance received for U.S. Appl. No. 13/458,830, mailed on Jul. 9, 2014, 8 pages.
Advisory Action received for U.S. Appl. No. 13/591,092, mailed on Jun. 6, 2013, 3 pages.
Final Office Action received for U.S. Appl. No. 13/591,092, mailed on Mar. 25, 2013, 22 pages.
Notice of Allowance received for U.S. Appl. No. 13/591,092, mailed on Feb. 21. 2014, 11 pages.
Office Action received for Canadian Patent Application No. 2,650,860, mailed on May 12, 2011, 2 pages.
Notice of Ailowance received for Canadian Patent Application No. 2,650,860, mailed on Apr. 2, 2013, 1 page.
Office Action received for Canadian Patent Application No. 2,737,704, mailed on Feb. 21, 2013, 3 pages.
Office Action received for Canadian Patent Application No. 2,760,840, mailed on Jul. 30, 2013, 4 pages.
Office Action received for Canadian Patent Application No. 2,760,840, mailed on Jan. 3, 2013, 3 pages.
Notice of Allowance received for Canadian Patent Application No. 2,762,985, mailed on Oct. 29, 2012, 1 page.
Office Action received for Australian Patent Application No. 2007248736, mailed on Dec. 1, 2009, 2 pages.
Office Action received for Chinese Patent Application No. 201110097994.X, mailed on Mar. 27, 2013, 7 pages. English Translation Only.
Office Action received for Australian Patent Application No. 2011348161. issued on Feb. 21, 2014, 4 pages.
Office Action received for Chinese Patent Application No. 201210287568.7, mailed on Jul. 26. 2013, 3 pages. English Translation Only.
Office Action received for Australian Patent Application No. 2013205681, mailed on Jun. 27, 2013. 4 pages.
Office Action received for Indian Patent Application No. 5933/CHENP/2008, mailed on Oct. 29, 2010, 2 pages.
Adapa et al., "Pelleting Characteristics of Selected Biomass With and Without Steam Explosion Pretreatment". Int. J. Agric. & Biol Eng, vol. 3, No. 3, Sep. 2010, pp. 62-79.
Allan et al., "Replacement of Fish Meal in Diets for Australian Silver Perch, *Bidyanus bidyanus*: I. Digestibility Of Alternative Ingredients". Aquaculture, vol. 186, No. 3-4, Jun. 2000, pp. 293-310.
Balan et al., "Lignocellulosic Biomass Pretreatment Using AFEX". Biofuels: Methods and Protocols, Methods in Molecular Biology, Chapter 5, vol. 581, 2009. pp. 61-77.
Balan et al., "Mushroom Spent Straw: A Potential Substrate for an Ethanol-Based Biorefinery", Journal of Industrial Microbiology and Biotechnology, vol. 35, No. 5, Society for Industrial Microbiology, 2008, pp. 293-301.
Baldrian, et al., "Variability of Laccase Activity in the White-Rot Basidiomycete *Pleurotus ostreatus*", Folia Microbiologica, vol. 47, No. 4, 2002, pp. 385-390.
Bals et al., "Enzymatic Hydrolysis of Distiller's Dry Grain and Solubles (DDGS) Using Ammonia Fiber Expansion Pretreatment", Energy & Fuels 2006, vol. 20, No. 6, American Chemical Society, Oct. 2006, pp. 2732-2736.

Beale et al., "Leaf Photosynthesis in the C4-Grass *Miscanthus x giganteus*, Growing in the Cool Temperate Climate of Southern England", Journal of Experimental Botany, vol. 47, No. 295, Feb. 1996, pp. 267-273.
Belyea et al., "Element Concentrations of Dry-Grind Corn-Processing Streams", Applied Biochemistry and Biotechnology, vol. 134, No. 2, Humana Press, 2006, pp. 113-128.
Betschart et al., "Extractability and Solubility of Leaf Protein", J. Agric. Food Chem., vol. 21, No. 1, 1973, pp. 60-65.
Boluk. Yaman, "Acid-Base Interactions and Swelling of Cellulose Fibers in Organic Liquids". Cellulose, vol. 12, No. 6, Springer Netherlands, Dec. 2005, pp. 577-593.
Bothast et al., "Biotechnological Processes for Conversion of Corn into Ethanol", Appl Microbiol Biotechnol, vol. 67, No. 1, Springer-Verlag, Apr. 2005, pp. 19-25.
Christian et al., "Degradation of Xenobiotic Compounds by Lignin-Degrading White-Rot Fungi: Enzymology and Mechanisms Involved", Indian Journal of Experimental Biology, vol. 43, Apr. 2005, pp. 301-312.
Chundawat et al., "Effect of Particle Size Based Separation of Milled Corn Stover on AFEX Pretreatment and Enzymatic Digestibility". Biotechnology and Bioengineering, vol. 96, No. 2, Feb. 1, 2007, pp. 219-231.
Chundawat et al., "Multi-scale Visualization and Characterization of Lignocellulosic Plant Cell Wall Deconstruction During Thermochemical Pretreatment", Energy & Environmental Science, No. 4, 2011, pp. 973-984.
Clifton-Brown et al., "Performance of 15 *Miscanthus* Genotypes at Five Sites in Europe", Agronomy Journal, vol. 93, No. 5, 2001, pp. 1013-1019.
Cohen et al., "Biotechnological Applications and Potential of Wood-Degrading Mushrooms of the Genus *Pleurotus*", Appl Microbial Biotechnol, vol. 58, Feb. 2002, pp. 582-591.
Non-Final Office Action received for U.S. Appl. No. 11/719,158, mailed on Apr. 1, 2009, 6 pages.
Final Office Action received for U.S. Appl. No. 11/719,158, mailed on Aug. 4, 2010, 7 pages.
Notice of Allowance received for U.S. Appl. No. 11/719,158, mailed on Jan. 6, 2011, 4 pages.
Non-Final Office Action received for U.S. Appl. No. 12/791,703, mailed on Jul. 27, 2012, 7 pages.
Notice of Allowance received for U.S. Appl. No. 12/791,703, mailed on Nov. 8, 2012, 8 pages.
International Search Report and Written Opinion for PCT Patent Application No. PCT/US2011/038524, mailed on Feb. 9, 2012, 7 pages.
Kawasaki et al., "Deodorization of Ammonia by Coffee Grounds", Journal of Oleo Science, vol. 55, No. 1, 2006, pp. 31-35.
Selig et al., "Enzymatic Saccharification of Lignocellulosic Biomass", National Renewable Energy Laboratory, Technical Report, NREL/TP-510-42629, Mar. 21, 2008, 8 pages.
Bals et al. "Evaluating the Impact of Ammonia Fiber Expansion (AFEX) Pretreatment Conditions on the Cost of Ethanol Production", Bioresource Technology, vol. 102, 2011, pp. 1277-1283.
International Search Report received for PCT Patent Application No. PCT/US2013/037935, mailed on Jul. 19, 2013, 4 pages.
Sendich et al. "Recent Process Improvements for the Ammonia Fiber Expansion (AFEX) Process and Resulting Reductions in Minimum Ethanol Selling Price", Bioresource Technology, vol. 99, 2008, pp. 8429-8435.
Viable Herbal Solutions, "Production Techniques to Produce Herbal Extracts", available Online at <http://viablehealth.com/herb/herbs42.html>, Prior to Dec. 22, 2010, 4 pages.
Teymouri et al., "Hydrolysis of Ground and Unground AFEX Treated Corn Stover with Different Combinations of Cellulase and Xylanase", 27th Symposium on Biotechnology for Fuels and Chemicals, May 1-4, 2005, 21 pages.
Mantanis et al., "Swelling of Compressed Cellulose Fiber Webs in Organic Liquids", Cellulose, vol. 2, No. 1, Kluwer Academic Publishers, 1995. pp. 1-22.
Martinez et al., "Biodegradation of Lignocellulosics: Microbial, Chemical, and Enzymatic Aspects of the Fungal Attack of Lignin", International Microbiology. vol. 8, 2005, pp. 195-204.

(56) References Cited

OTHER PUBLICATIONS

Mosier et al., "Optimization of pH Controlled Liquid Hot Water Pretreatment of Corn Stover", Bioresource Technology, vol. 96, 2005, pp. 1986-1993.
Obodai et al,. "Comparative Study on the Growth and Yield of *Pleurotus ostreatus* Mushroom on Different Lignocellulosic By-Products". Journal of Industrial Microbiology and Biotechnology, vol. 30, No. 3, Society for Industrial Microbiology, 2003, pp. 146-149.
O'Connor, James J., "Amrnonia Explosion Pulping: A New Fiber Separation Process", Tappi, vol. 55, No. 3, Mar. 1972, pp. 353-358.
Ohara, H., "Biorefinery", Applied Microbiology and Biotechnology, Springer-Verlag, vol. 62, No. 5-6, Oct. 2003. pp. 474-477.
Ordonez et al., "Obtaining a Protein Concentrate from Integral Defatted Sunflower Flour", Bioresource Technology, vol. 78, No. 2, Elsevier Science Ltd., 2001, pp. 187-190.
Ozturk et al,. "Splitting Tendency of Cellulosic Fibers. Part 2: Effects of Fiber Swelling in Alkali Solution", Cellulose, vol. 13, No. 4, Springer Netherlands, Aug. 2006. pp. 403-409.
Pandey et al., "Economic Utilization of Crop Residues for Value Addition: A Futuristic Approach", Journal of Scientific & Industrial Research, vol. 59, Jan. 2000, pp. 12-22.
Park et al., "Investigation and Optimization of the Factors Influencing Sorghum Protein Extraction", Journal of Agricultural and Food Chemistry, vol. 51, No. 24, American Chemical Society. Oct. 2003, pp. 7050-7054.
Paul et al., "Liquid-Vapor Interfacial Properties of Water-Ammonia Mixtures: Dependence on Ammonia Concentration", J. Chem. Phys., vol. 123, No. 17, 2005, 10 pages.
International Preliminary Report on Patentability received for PCT Patent Application No. PCT/US2007/010410, mailed on Dec. 12, 2008, 5 pages.
International Search Report and Written Opinion received for PCT Patent Application No. PCT/US2007/010410, mailed on Jun. 10, 2008, 5 pages.
International Preliminary Report on Patentability received for PCT Patent Application No. PCT/US2007/010415, mailed on Aug. 5, 2008. 6 pages.
International Search Report and Written Opinion received for PCT Patent Application No. PCT/US2008/011488, mailed on Jan. 8, 2009, 6 pages.
International Search Report and Written Opinion received for PCT Patent Application No. PCT/US2011/061617, mailed on Jun. 8, 2012. 10 pages.
International Preliminary Report on Patentability received for PCT Application No. PCT/US2011/066868, mailed on Jul. 4, 2013, 5 pages.
International Search Report and Written Opinion received for PCT Application No. PCT/US2012/059898, mailed on Jul. 26, 2013, 11 pages.
International Search Report and Written Opinion received for PCT Patent Application No. PCT/US2013/028689 mailed on Jun. 4, 2013, 5 pages.
Piva et al., "Detoxification Methods of Aflatoxins. A Review", Nutrition Research, vol. 15, Issue 5, May 1995, pp. 767-776.
Poppe J "Use of Agricultural Waste Materials in the Cultivation of Mushrooms", Science and Cultivation of Edible Fungl, vol. 1-2, 2000, pp. 3-23.
Prevot-D'Alvise et al., "Deveopment of a Pilot Process for the Production of Alfalfa Peptide Isolate", Journal of Chemical Technology and Biotechnology, vol. 78, Issue 5, May 2003, pp. 518-528.
Ragauskas et al., "The Path Forward for Biofuels and Biomaterials", Science, vol. 311, No. 5760, Jan. 27, 2006, pp. 484-489.
Rajagopalan et al., "Enhancing Profitability of Dry Mill Ethanol Planta", Applied Biochemistry and Biotechnology, vol. 120, No. 1, Humana Press, 2005, pp. 37-50.
Rausch et al., "The Future of Coproducts from Corn Processing", Applied Biochemistry and Biotechnology, vol. 128, Humana Press Inc., 2006, pp. 47-86.
Renewable Fuels Association, "From Niche to Nation: Ethanol Industry Outlook 2006", RFA Industry Outlook, 2006, 24 pages.
Rijal et al., "Combined Effect of Pelleting and Pretreatment on Enzymatic Hydrolysis of Switchgrass", Bioresource Technology, vol. 116, 2012, pp. 36-41.
Rollin et al., "Increasing Cellulose Accessibility is More Important Than Removing Lignin: A Comparison of Cellulose Solvent-Based Lignocellulose Fractionation and Soaking in Aqueous Ammonia", Biotechnology and Bioengineering, vol. 108, No. 1, Jan. 2011. pp. 22-30.
Rosa et al., "integrated Production of Ethanol Fuel and Protein from Coastal Bermudagrass", Applied Biochemistry and Biotechnology, vols. 45/46, No. 1, Humana Press Inc., 1994, pp. 483-497.
Saha, Badal C., "Hemicellulose Bioconversion", Journal of Industrial Microbiology and Biotechnology, vol. 30, No. 5, May 2003, pp. 279-291.
Sanchez et al., "Biodegradation of Viticulture Wastes by *Pleurotus*: A Source of Microbial and Human Food and Its Potential Use in Animal Feeding", J. Agric. Food Chem., vol. 50, No. 9, American Chemical Society, Apr. 24, 2002, pp. 2637-2542.
Sanderson et al "Switchgrass as a Sustainable Bioenergy Crop", Bioresource Technology, Elsevier Science Limited, vol. 56, No. 1, Apr. 1996, pp. 83-93.
Sarikaya et al., "Solid-State Fermentation of Lignocellulosic Plant Residues from *Brassica napus* by *Pleurotus ostreatus*" Applied Biochemistry and Biotechnology, vol. 82, No. 1, Humana Press, Oct. 1999, pp. 1-15.
Singh et al., "Composting of a Crop Residue through Treatment with Microorganisms and Subsequent Vermicomposting", Bioresource Technology, vol. 85. No. 2, Nov. 2042, pp. 107-111.
Sluiter et al., "Determination of Structural Carbohydrates and Lignin in Biomass", National Renewable Energy Laboratory, Laboratory Analytical Procedure (LAP), Technical Report, NREL/TP-510-42618, Apr. 25, 2008, 17 pages.
Sokhansanj et al, "Biomass Densification—Cubing Operation and Costs for Corn Stover", Applied Engineering in Agriculture, vol. 20, No. 4, 2404, pp. 495-499.
Somerville et al., "Toward a Systems Approach to Understanding Plant Cell Walls", Science, vol. 306, No. 5705, Dec. 24, 2004, pp. 2206-2211.
Steele et al., "Enzyme Recovery and Recycling Following Hydrolysis of Ammonia Fiber Explosion—Treated Corn Stover", Applied Biochemistry and Biotechnology, vol. 121-124, Nos. 1-3, Humana Press, 2005, pp. 901-910.
Sukumaran et al., "Cellutase Production Using Biomass Feed Stock and its Application in Lignocellulose Saccharification for Bio-Ethanol Production", Renewable Energy, Elsevier Ltd., vol. 34, No. 2, Feb. 2009, pp. 421-424.
Sulbaran-De-Ferrer et al., "Enzymatic Hydrolysis of Ammonia-Treated Rice Straw", Applied Biochemistry and Biotechnology, vol. 105-108, 2003, pp. 155-164.
Sun et al., "Hydrolysis of Lignocellulosic Materials for Ethanol Production: A Review", Bioresouce Technology, vol. 83, No. 1, 2002, pp. 1-11.
Sunopta Bioprocess Group, "SunOpta BioProcess Solutions", Sun Opta, 2838 Bovaird Drive West, Norval, Ontario L7A OH2, bioprocess@sunopta.com, 2007, 20 pages.
Suto et al "Induction and Catabolite Repression Mechanisms of Cellulase in Fungi", Journal of Bioscience and Bioengineering, vol. 92, No. 4, Elsevier B.V., 2001, pp. 305-311.
Tabil et al., "Biomass Feedstock Pre-Processing—Part 1: Pre-Treatment", Chapter 18, Biofuel's Engineering Process Technology, Aug. 2011, pp. 411-438.
Taniguchi et al., "Evaluation of Pretreatment with *Pleurotus ostreatus* for Enzymatic Hydrolysis of Rice Straw", Journal of Bioscience and Bioengineering, vol. 100, No. 6, Elsevier B.V., Dec. 2005, pp. 637-643.
Theerarattananoon et at., "Effects of the Pelleting Conditions on Chemical Composition and Sugar Yield of Corn Stover, Big Bluestem, Wheat Straw, and Sorghum Stalk Pellets", Bioprocess Biosyst. Eng., vol. 35, No. 4, May 2012, pp. 615-623.
Tolan, Jeffrey S., "logen's Demonstration Process for Producing Ethanol from Cellulosic Biomass", Chapter 9, Fuel-oriented

(56) References Cited

OTHER PUBLICATIONS

Biorefineries, Biorefineries—Industrial Processes and Products, WILEY-VCH Verlag GmbH & Co., 2006, pp. 193-208.
Turner et al., "Disruption of Forage Structure with an Ammonia Fiber Explosion Process", Proceedings, Western Section, American Society of Animal Science, vol. 41, 1990, pp. 494-497.
Uraki et al., "Body Temperature-Responsive Gels Derived from Hydroxypropylcellulose Bearing Lignin II: Adsorption and Release Behavior", Cellulose, vol. 13, No. 3, Springer Netherlands, Jun. 2006, pp. 225-234.
Urribarri et al., "Leaf Protein from Ammonia-Treated Dwarf Elephant Grass (*Pennisetum purpureum* Schum cv. Mott)", Applied Biochemistry and Biotechnology, Hurnana Press Inc, vols. 121-124, 2005, pp. 721-730.
Van Horn et al., "Complete Rations for Growing Dairy Replacements Utilizing By-Product Feedstuffs". Journal of Dairy Science, vol. 63, 1980, pp. 1465-1474.
Vrije et al., "Pretreatment of Miscanthus for Hydrogen Production by *Thermotoga elfii*", International Journal of Hydrogen Energy, vol. 27, Nos. 11-12, 2002, pp. 1381-1390.
Walter, Arnaldo, "Industrial Uses of Biomass Energy: New Technologies for Modern Biomass Energy Carriers", Taylor & Francis, Chapter 9, edited by Rosillo-Calle F., Bajay SV, Rothman H, 2000, 57 pages.
Wang et al., "Cost Estimates and Sensitivity Analyses for the Ammonia Fiber Explosion Process", Applied Biochemistry and Biotechnology, vol. 70-72, No. 1, 1998. pp. 51-66.
Wheals et al., "Fuel Ethanol after 25 Years", Trends in Biotechnology, Department of Biology and Biochemistry, vol. 17, No. 12, Dec. 1999, pp. 482-487.
Williams et al., "An Initial Assessment of Spent Mushroom Compost as a Potential Energy Feedstock", Bioresource Technology, vol. 79, No. 3, Sep. 2001, pp. 227-230.
Wyman et al., "Comparative Sugar Recovery Data From Laboratory Scale Application of Leading Pretreatment Technologies to Corn Stover", Bioresource Technology, vol. 96, No. 18, 2005, pp. 2026-2032.
Wyman et al., "Coordinated Development of Leading Biomass Pretreatment Technologies", Bioresource Technology, vol. 96, No. 18, 2005, pp. 1959-1966.
Ye et al., "Improving Accessibility and Reactivity of Cellulose of Annual Plants for the Synthesis of Methylcellulose", Cellulose, vol. 12, No. 5. Oct. 2005, pp. 507-515.
Zhang et al., "A Transition from Cellulose Swelling to Cellulose Dissolution by A-Phosphoric Acid: Evidence from Enzymatic Hydrolysis and Supramolecular Structure", Biomacromolecules, vol. 7, No. 2, ACS Publication, Feb. 2006, pp. 644-648.
Zhang et al., "Oyster Mushroom Cultivation with Rice and Wheat Straw", Bioresource Technology. vol. 82. No. 3, May 2002, pp. 277-284.
Zhang et al., "Toward an Aggregated Understanding of Enzymatic Hydrolysis of Cellulose: Noncomplexed Cellulase Systems", Biotechnology and Bioengineering, vol. 88, No. 7, Dec. 30, 2004, pp. 797-824.
Zhong et al., "Optimization of Enzymatic Hydrolysis and Ethanol Fermentation from AFEX-Treated Rice Straw", Applied Microbiology and Biotechnology, vol. 84, No. 4, Springer-Verlag, Sep. 2009, pp. 667-676.
Zhou et al., "Gene Integration and Expression and Extracellular Secretion of *Erwinia chrysanthemi* Endoglucanase CelY (celY) and CelZ (celZ) in Ethanologenic *Klebsiella oxytoca* P2†", Applied and Environmental Microbiology, vol. 67, No. 1, American Society for Microbiology, 2001, pp. 6-14.
Cosgrove, Daniel J., "Growth of the Plant Cell Wall", Nature Reviews Molecular Cell Biology, vol. 6, Nov. 2005, pp. 850-861.
Dale et al., "Extrusion Processing for Ammonia Fiber Explosion (AFEX)", Applied Biochemistry and Biotechnology, vol. 77-79, 1999, pp. 35-45.

Dale et al., "Fermentation of Lignocellulosic Materials Treated by Ammonia Freeze-Explosion", The Society for Industrial Microbiology, 1985, Reprinted from vol. 26 of Developments in Industrial Microbiology, pp. 223-233.
El-Adawy et al., "Nutritional Potential and Functional Properties of Sweet and Bitter Lupin Seed Protein Isolates", Food Chemistry, vol. 74, No. 4, Elsevier Science Ltd., 2001, pp. 455-462.
Energy Policy Act of 2005 Public Law, "Public Law 109-58", 109th Congress, 1st Session, Aug. 8, 2005, 11 pages.
Erickson, David R., "Edible Fats and Oils Processing: Basic Principles and Modern Practices", AOCS Press, 1990, 6 pages.
"U.S. Fuel Ethanol Industry Biorefineries and Production Capacity", available online at <http://www.ethanolrfa.org/industry/locations>, Nov. 18, 2008, 4 pages.
Fernandez et al., "Protein Extraction from *Atriplex lampa* Leaves: Potential Use as Forage for Animals used for Human Diets", Plant Foods for Human Nutrition, Kluwer Academic Publishers, vol. 54, No. 3, 1999, pp. 251-259.
Ferrer et al., "Increasing Nutrient Availability of Feather Meal for Ruminants and Non-Ruminants Using an Ammonia Pressurisation/ Depressurisation Process", Journal of the Science of Food and Agriculture, vol. 79 Society of Chemical Industry, 1999, pp. 828-832.
Ferrer et al,. "Optimizing Ammonia Pressurization/Depressurization Processing Conditions to Enhance Enzymatic Susceptibility of Dwarf Elephant Grass", Applied Biochemistry and Biotechnology, Humana Press Inc., vol. 34-36, No. 1-9, Mar. 2000, pp. 163-179.
Fiorentini et al., "Pilot Plant Production of an Edible Alfalfa Protein Concentrate", Journal of Food Science, vol. 46, No. 5, Sep. 1981, pp. 1514-1517.
Foster et al., "Enzymatic Hydrolysis of Ammonia-Treated Sugar Beet Pulp", Applied Biochemistry and Biotechnology, Humana Press Inc., vol. 91-93, 2001, pp. 269-282.
Fulks et al.. "A Review of Solid Materials as Alternative Ammonia Sources for Lean NOx Reduction with SCR", Technical Paper No. 9-2009-01-0907, SAE International, 2009, 13 pages.
Gao et al.. "Mixture Optimization of Six Core Glycosyl Hydrolases for Maximizing Saccharification of Ammonia Fiber Expansion (AFEX) Pretreated Corn Stover", Bioresource Technology, vol. 101, Issue 8, Apr. 2010, pp. 2770-2781.
Gollapalli at al., "Predicting Digestibility of Ammonia Fiber Explosion (AFEX)-Treated Rice Straw", Applied Biochemistry and Biotechnology, Humana Press Inc., vol. 98-100. 2002, pp. 23-35.
Gray et al., "Bioethanol", Current Opinion in Chemical Biology, Elsevier, vol. 10, 2006. pp. 141-146.
Greene et al.. "Growing Energy: How Biofuels Can Help End America's Oil Dependence", Natural Resources Defense Council, Dec. 2004, 86 pages.
Hahn-Hagerdal et al., "Bio-Ethanol—The Fuel of Tomorrow from the Residues of Today", Trends in Biotechnology, vol. 24, No. 12, Elsevier Ltd., Dec. 2006, pp. 549-556.
Hanchar et al., "Separation of Glucose and Pentose Sugars by Selective Enzyme Hydrolysis of AFEX-Treated Corn Fiber", Applied Biochemistry and Biotechnology, vols. 137-140, Nos. 1-12, Humana Press Inc., 2007, pp. 313-326.
Heaton et al., "A Quantitative Review Comparing the Yields of Two Candidate $C_4$ Perennial Biomass Crops in Relation to Nitrogen, Temperature and Water". Biomass and Bioenergy, vol. 27, No. 1, Jul. 2004, pp. 21-30.
Heaton et al., "*Miscanthus* for Renewable Energy Generation: European Union Experience and Projections for Illinois", Mitigation and Adaptation Strategies for Global Change, vol. 9, No. 4, Oct. 2004, pp. 433-451.
Holtzapple at al., "The Ammonia Freeze Explosion (AFEX) Process: A Practical Lignocellulose Pretreatment", Applied Biochemistry and Biotechnology. vols. 28/29, No. 1, 1991, pp. 59-74.
Houghton et al.. "Fungal Upgrading of Wheat Straw for Straw-Thermoplastics Production", Applied Biochemistry and Biotechnology, vol. 113-116, Humana Press Inc., 2004, pp. 71-93.
Israilides et al., "Bio-technologies of Recycling Agro-industrial Wastes for the Production of Commercialiy Important Fungal Polysaccharides and Mushrooms", Biotechnology and Genetic Engineering Reviews, vol. 20, Dec. 2003, pp. 247-259.

(56) References Cited

OTHER PUBLICATIONS

Jeoh et al., "Cooperative and Competitive Binding in Synergistic Mixtures of *Thermobifida fusca* Cellulases Ce15A, Ce16B, and Ce19A", Biotechnol. Prog., vol. 18, No. 4, 2002, pp. 760-769.

Jin et al., "A Novel Integrated Biological Process for Cellulosic Ethanol Production Featuring High Ethanol Productivity, Enzyme Recycling and Yeast Cells Reuse", Energy & Environmental Science, The Royal Society of Chemistry, No. 5, 2012, 8 pages.

Jin et al., "Two-Step SSCF to Convert AFEX-Treated Switchgrass to Ethanol using Commercial Enzymes and *Saccharomyces cerevisiae* 424A (LNH-ST)", Bioresource Technology, vol. 101, No. 21, 2010, pp. 8171-8178.

Kamm et al., "Principles of Biorefineries", Applied Microbiology and Biotechnology. vol. 64, No. 2, Springer-Verlag, Apr. 2004, pp. 137-145.

Karunanandaa et al., "Botanical Fractions of Rice Straw Colonized by White-Rot Fungi: Changes in Chemical Composition and Structure", Animal Feed Science Technology, vol. 55, 1995, pp. 179-199.

Keller et al., "Microbial Pretreatment of Biomass: Potential for Reducing Severity of Thermochemical Biomass Pretreatment", Applied Biochemistry and Biotechnology, vols. 105-108, Humana Press Inc., 2003, pp. 27-41.

Kim et al.. "Enhancement of the Enzymatic Digestibility of Waste Newspaper Using Tween", Applied Biochemistry and Biotechnology, vols. 129-132, Humana Press Inc., 2006, pp. 486-495.

Kim et al., "Lime Pretreatment and Enzymatic Hydrolysis of Corn Stover", Bioresource Technology, vol. 96, No. 18, Mar. 10, 2005, pp. 1994-2006.

Kim et al.. "Pretreatment and Fractionation of Corn Stover by Ammonia Recycle Percolation Process", Bioresource Technology, vol. 96, No. 18, 2005, pp. 2007-2013.

Kim et al., "Pretreatment of Corn Stover by Low-Liquid Ammonia Recycle Percolation Process", Applied Biochemistry and Biotechnolology, vol. 133, Apr. 2006, pp. 41-57.

Knauf et al.. "Lignocellulosic Biomass Processing: A Perspective", International Sugar Journal, vol. 106, No. 1263, 2004, pp. 147-150.

Kumar et al.. "Does Densification influence the Steam Pretreatment and Enzymatic Hydrolysis of Softwoods to Sugars?", Bioresource Technology, vol. 121, Oct. 2012, 38 pages.

Ladisch et al., "Building a Bridge to the Ethanol industry—Follow-Up Project", National Renewable Energy Laboratory, Apr. 2003, 36 pages.

Lau et al., "Cellulosic Ethanol Production from AFEX-trealed Corn Stover Using *Saccharomyces cerevisiae* 424A (LNH-ST)", PNAS, vol. 106, No. 5, Feb. 3, 2009, pp. 1368-1373.

Lau et al., "Comparing the Fermentation Performance of *Escherichia coli* KO11, *Saccharomyces cerevisiae* 424A (LNH-ST) and *Zymomonas mobilis* AX101 for Cellulosic Ethanol Production", Biotechnology for Biofuels, vol. 3, No. 11, 2010, 10 pages.

Lau at al., "Ethanol Fermentation of *E. coli* K011 in Hydrolysate from AFEX-treated Corn Stover", Biomass Conversion Research Laboratory, Department of Chemical Engineering and Materials Science, Michigan State University, Prior to Dec. 22, 2010, 1 page.

Lau at al., "The Impacts of Pretreatment on the Fermentability of Pretreated Lignocellulosic Biomass: A Comparative Evaluation between Ammonia Fiber Expansion and Dilute Acid Pretreatment", Biotechnology for Biofuels. vol. 2, No. 30, 2009, 11 pages.

Laureano-Perez et al., "Understanding Factors that Limit Enzymatic Hydrolysis of Biomass", Characterization of Pretreated Corn Stover, Applied Biochemistry and Biotechnology, vols. 121-124, Humana Press Inc., 2005, pp. 1081-1099.

Lin et al., "Ethanol Fermentation from Biomass Resources: Current State and Prospects", Applied Microbiology and Biotechnology, Springer-Verlag, vol. 69, No. 6., Feb. 2006, pp. 627-642.

Liu et al., "Partial Flow of Compressed-Hot Water through Corn Stover to Enhance Hemicellulose Sugar Recovery and Enzymatic Digestibility of Cellulose", Bioresource Technology, vol. 96, No. 18, 2005, pp. 1978-1985.

Lloyd et al., "Combined Sugar Yields for Dilute Sulfuric Acid Pretreatment of Corn Stover Followed by Enzymatic Hydrolysis of the Remaining Solids", Bioresource Technology, vol. 96, No. 18, Dec. 2005, pp. 1967-1977.

Lovrien et al., "Assays for Total Protein", Current Protocols in Protein Science, John Wiley & Sons. Inc., 1995, 24 pages.

Lu et al., "Cellulase Adsorption and an Evaluation of Enzyme Recycle During Hydrolysis of Steam-Exploded Softwood Residues", Applied Biochemistry and Biotechnology, vols. 98-100, Humana Press Inc., 2002, pp. 641-654.

Madakadze et al., "Cutting Frequency and Nitrogen Fertilization Effects on Yield and Nitrogen Concentration of Switchgrass in a Short Season Area", Crop Science, vol. 39, No. 2, Mar.-Apr. 1999, pp. 552-557.

Mani et al., "Economics of Producing Fuel Pellets from Biomass", Applied Engineering in Agriculture, vol. 22, No. 3, American Society of Agricultural and Biological Engineers, pp. 421-426.

\* cited by examiner

METHODS FOR PRETREATING BIOMASS

CROSS REFERENCE TO RELATED APPLICATIONS

This application is a continuation-in-part of U.S. application Ser. No. 11/901,336 filed Sep. 17, 2007, entitled PROCESS FOR THE TREATMENT OF LIGNOCELLULOSIC BIOMASS, now issued as U.S. Pat. No. 7,915,017, which is a continuation-in-part of International Application No. PCT/US07/10415, filed on Apr. 30, 2007, which claims the benefit of U.S. Provisional Application Ser. No. 60/796,375 filed May 1, 2006, the entire contents of which applications are incorporated herein in their entirety. This application also is a continuation of International Application No. PCT/US2010/035826, filed on May 21, 2010, entitled METHODS FOR PRETREATING BIOMASS, which claims the benefit of U.S. Provisional Application No. 61/180,308, filed on May 21, 2009, the entire contents of which applications are incorporated herein in their entirety.

STATEMENT OF GOVERNMENT RIGHTS

This invention was made with government support under XCO-3-33033-01 awarded by the U.S. Department of Energy and under 00-52104-9663 awarded by the U.S. Department of Agriculture. The government has certain rights in the invention.

FIELD OF THE INVENTION

This invention is in the field of biomass processing, in particular alkaline pretreatment of biomass.

BACKGROUND OF THE INVENTION

With an ever increasing demand for petroleum, there has been growing interest in renewable feedstocks for manufacturing bioethanol (1). Based on recent economic analysis, a modern biorefinery will utilize about 2000 tons/day of lignocellulosic biomass ("biomass") for producing biofuels and biochemicals (2). Lignocellulosic fibers comprise a complex network of cellulose, hemicellulose and lignin (3-4) producing a compact matrix, that is difficult to hydrolyze due to poor enzyme accessibility. To improve accessibility of enzymes to the interwoven polysaccharides, a thermochemical treatment (i.e., a "pretreatment") is typically necessary before enzymatic hydrolysis.

Different types of feed stocks are readily available for making biofuels. Such feedstocks include agricultural residues, woody biomass, municipal waste, oilseeds/cakes and sea weeds. Commercially available oil seed cakes include canola, sunflower, sesame, peanut, palm oil, Jatropha and soybean. At present these different agricultural residues and oil cakes are either used as animal feed, biocompost materials or are land filled. Grasses and oilseed cakes/meals are rich in protein, fiber and other nutrients. It might be possible to utilize the fiber rich portion of the feed stock to make bioethanol by utilizing a suitable thermochemical pretreatment, enzymatic hydrolysis and fermentation process. Economical pretreatment of feed stocks in a continuous manner is quite challenging. For several leading pretreatment processes such as dilute acid, concentrated ammonia (AFEX)™ (hereinafter "AFEX"), steam explosion, and organosolv, a detailed economic analysis has been reported (5).

A wide variety of methods (e.g., concentrated or dilute acids or bases, high temperatures, radiation of various forms) have been used to pretreat lignocellulosic biomass to extract structural carbohydrates to be used to obtain monosaccharides for many different uses. The goal of these pretreatments is to increase the rate and/or yield at which the monosaccharides are subsequently obtained from the structural carbohydrates by chemical or biochemical means, such as acid catalysis, enzymatic catalysis, fermentation or animal digestion. In general, these pretreatments have fallen short of desired economic and technical performance for several reasons: 1) many pretreatments degrade some of the sugars, e.g., to acids or aldehydes, thus reducing yields and inhibiting subsequent biological conversion of the remaining sugars; 2) when chemicals are used in the pretreatment, it is frequently difficult to recover these chemicals at reasonable cost; 3) residual chemicals can negatively affect downstream conversion operations; and 4) the effectiveness of many pretreatments is limited so that the ultimate conversions of structural carbohydrates obtained, independent of lost yield by sugar degradation reactions, is inadequate for competitive process economics. Thus, there are many prior art methods, and they have numerous drawbacks, including those outlined above.

Sufficiently inexpensive monosaccharides from renewable plant biomass can become the basis of chemical and fuels industries, replacing or substituting for petroleum and other fossil feedstocks. Highly reactive lignocellulosic biomass can also become the basis of improved animal feeds, particularly for ruminant animals. Effective, economical pretreatments are required to make these monosaccharides available at high yield and acceptable cost.

The prior art in the pretreatment of plant biomass with anhydrous liquid ammonia or ammonium hydroxide solutions is extensive. Illustrative are the following patents and literature references: U.S. Pat. No. 4,600,590 to Dale; U.S. Pat. No. 4,644,060 to Chou; U.S. Pat. No. 5,037,663 to Dale; U.S. Pat. No. 5,171,592 to Holtzapple et al.; U.S. Pat. No. 5,865,898 to Holtzapple et al.; U.S. Pat. No. 5,939,544 to Karsents et al.; U.S. Pat. No. 5,473,061 to Bredereck et al.; U.S. Pat. No. 6,416,621 to Karstens; U.S. Pat. No. 6,106,888 to Dale et al; U.S. Pat. No. 6,176,176 to Dale et al; U.S. Patent Application No. 2007/0031918, filed Apr. 12, 2006; Felix, A., et al., Anim. Prod. 51 47-61 (1990); and Waiss, A. C., Jr., et al., Journal of Animal Science 35 No. 1, 109-112 (1972). All of these patents and publications are incorporated herein in their entireties.

Ammonia fiber expansion (AFEX) is a leading alkaline pretreatment process that modifies the cell wall ultra-structure without physically extracting lignin and hemicellulose into a separate liquid stream. In addition, the inhibitory compounds formed during the ammonia pretreatment process are insignificant compared to dilute acid pretreatment which play an important inhibitory role during downstream biological processing. The primary advantage of using ammonia during pretreatment is relatively easy recovery and reusability of ammonia due to its high volatility. Close inspection of various ammonia based pretreatments, reveal that ammonia was either used in its liquid state (30-99% ammonia concentration) (6-11), supercritical state (12) or as dilute ammonium hydroxide (0.1-28%) (13-14). Ammonia recycled percolation (ARP) (15) and AFEX pretreatment are leading ammonia based biomass pretreatment technologies. However, most current pretreatment processes rely on pretreating the biomass using a largely liquid pretreatment medium (with varying ammonia concentrations, 0.1-99%).

In particular, AFEX represents a unique and effective pretreatment for biologically converting lignocellulosic biomass to ethanol (Dale, B. E., 1986. U.S. Pat. No. 5,037,663; Dale, B. E., 1991. U.S. Pat. No. 4,600,590; Alizadeh, H., F. Teymouri, T. I. Gilbert, B. E. Dale, 2005. Pretreatment of Switchgrass by Ammonia Fiber Explosion. Applied Biochemistry and Biotechnology, 121-124:1133-1141; Dale, B. E., 1991. U.S. Pat. No. 4,600,590; Dale, B. E., 1986. U.S. Pat. No. 5,037,663). In AFEX pretreatment, lignocellulosic biomass is exposed to concentrated ammonia at elevated pressures sufficient to maintain ammonia in a liquid phase at moderate temperatures (e.g. around 100° C.). Residence times in the AFEX reactor are generally less than 30 minutes. To terminate the AFEX reaction, the pretreated biomass is depressurized (flashed). The AFEX process is not and has never been limited to the application of anhydrous ammonia with AFEX. Some water is always initially present with the biomass and sometimes water is added to the biomass, so that any anhydrous ammonia is immediately converted into a concentrated ammonia water mixture on beginning the AFEX treatment. However, a detailed exploration of how ammonia and water are best combined with each other and with the biomass to achieve effective pretreatment has never been performed.

Recovery of ammonia used in AFEX pretreatment is a key objective when integrating AFEX into a broader biomass conversion process design. The existing ammonia recovery design (Eggeman, T. 2001. Ammonia Fiber Explosion Pretreatment for Bioethanol Production, National Renewable Energy Laboratory (NREL) Subcontract No. LCO-1-31055-01), which is depicted in FIG. 1, calls for compressing ammonia, which is vaporized as a result of the flash operation, and separating ammonia that remains in contact with the pretreated solids via evaporation in a dryer. The resulting vapor, which also contains water, is then delivered to a distillation column to concentrate the ammonia. The ammonia from the column is pumped up to pressure and, together with the compressed flash ammonia, is recycled to the AFEX reactor. FIG. 1 shows the existing ammonia recovery approach.

FIG. 1 shows the prior art system 10 including a closed AFEX reactor vessel 12 into which biomass, water and ammonia are introduced under pressure. Valve $V_1$ is used to release pressure from the vessel 12. The treated biomass is transferred to a heated dryer 14. The dried biomass is transferred out of the dryer 14 for subsequent treatment. Ammonia from the dryer 14 is condensed by condenser 22 and sent to slurry column 16. Water is removed and condensed by condenser 18. Ammonia is condensed in condenser 20 and recycled to the vessel 12. Ammonia gas is pressurized in a compressor 24, condensed and recycled into vessel 12.

In AFEX, anhydrous liquid ammonia is used to pretreat the biomass at relatively low temperatures (70-180° C.), intermediate residence times (15-45 min), low moisture (10-200% on dwb), and higher ammonia loading (1:1-3:1, wt of ammonia/wt of biomass). During conventional AFEX, due to gravity, the liquid ammonia flows to the bottom of the reactor. Some amount of the liquid reacts with water and forms ammonium hydroxide, while the remaining liquid is converted to gaseous ammonia (depending on the thermodynamic gas-liquid state within the reactor). Since biomass is a poor conductor of heat, it takes a longer residence time (typically 15-45 min) to achieve the desired temperature throughout the reactor. Mixing and uniform pretreatment during AFEX is a significant problem in the absence of a suitable impeller. Mixing solid slurries using propellers and helical impellers is energy intensive and not very effective in reducing mass and heat transfer limitations. In other words, the biomass which is in contact with ammonium hydroxide and is suitably preheated (i.e., typically biomass close to the walls or at the bottom of the reactor) is pretreated under better conditions, as compared to the bulk of the biomass in the reactor. Another major economic hurdle to the AFEX process is the expensive recovery step, where ammonia needs to be recovered after pretreatment as a gas, recompressed, separated from water and reused as anhydrous liquid ammonia. Also, it is difficult to conduct AFEX in a continuous manner using pressurized liquid ammonia as the pretreatment chemical. The expansive release of ammonia at the end of AFEX pretreatment is energy intensive, generating gaseous ammonia-water mixtures that could make it commercially prohibitive. Supercritical ammonia based pretreatments are much more energy intensive than AFEX, making them an economically less viable option.

It is obvious to one skilled in the art that the ammonia pretreatment and recovery processes generate ammonia and water mixtures of differing phases (gaseous and liquid), compositions and temperatures. These resulting ammonia and water mixtures can therefore potentially be combined with each other and with new biomass to be treated in many different compositions and phases (gas and liquid).

The problem is that some of these potential ammonia and water treatment processes may either produce relatively low biomass reactivity and/or may require large amounts of liquid ammonia or ammonium hydroxide solutions. The most effective approaches to combine recycled ammonia and water of different compositions and phases to produce a highly reactive biomass are not well-understood. The optimal order of addition of water, ammonia and ammonia-water mixtures, and their relative amounts, temperatures and concentrations, has not been sufficiently defined so as to produce acceptable biomass reactivity. Furthermore, methods for maintaining ammonia in effective contact with the biomass, so as to reduce the total amount of ammonia required, have not been described.

Examples of previous ammonia pretreatment processes are ARP and dilute ammonium hydroxide. These processes include: high pretreatment temperature (150-180° C.), long residence time (30-120 min), high pressure liquid recycle, separation of biomass into solid and liquid fraction (by separating hemicellulose and lignin from cellulose into liquid fraction), low solids loading, and neutralization and/or recovery needed for downstream processing. Traditionally used gaseous ammoniation includes long residence time (several hours to weeks), and is expensive and inconvenient to scale-up.

BRIEF SUMMARY OF THE INVENTION

The present invention provides a process for the treatment of a plant biomass to increase the reactivity of plant polymers, comprising hemicellulose and cellulose, which comprises: contacting the plant biomass, which has been ground and which contains varying moisture contents, with anhydrous ammonia in the liquid or vapor state, and/or concentrated ammonia:water mixtures in the liquid or vapor state, to obtain a mixture in which the ratio of ammonia (as $NH_3$) to dry biomass is between about 0.2 to 1 and 1.2 to 1, and the water to dry biomass ratio is between about 0.2 to 1.0 and 1.5 to 1, maintaining the mixture in a closed vessel at temperatures between about 50° C. and 140° C. for a period of time; rapidly releasing the pressure by releasing ammonia from the vessel to form a treated biomass; removing the treated plant biomass which has increased reactivity from the vessel. Preferably, the treated biomass is hydrolyzed with enzymes to produce sugars. Preferably, the treated biomass is extracted to remove lignin and other compounds that can interfere with the ability of enzymes to hydrolyze the treated biomass. Preferably, the treated biomass is extracted to remove lignin and other compounds that can interfere with the ability of microorganisms to ferment the treated biomass. Preferably, the ammonia is compressed by a mechanical means for reducing the volume in a headspace inside the closed vessel and thereby increasing the fraction of the total ammonia that is in the liquid phase. Preferably, nitrogen under pressure is introduced into a headspace of the vessel so as to increase the fraction of the total ammonia that is in the liquid phase. Preferably, particles of an inert solid material are introduced into the vessel so as to increase the fraction of the total ammonia that is in the liquid phase. Preferably, particles of a solid material selected from the group consisting of sand and iron filings are introduced into the vessel so as to increase the fraction of the total ammonia that is in the liquid phase. Preferably, the headspace (gas phase) of the reactor vessel is connected with the headspace of an appropriate ammonia storage vessel so as to increase the fraction of the total ammonia that is in the liquid phase. Preferably, the treated biomass is hydrolyzed with enzymes to produce sugars and wherein the sugars are fermented by a microorganism to produce a fermentation product. Preferably, the treated biomass is fermented by a microorganism to produce a fermentation product without a separate sugar production step. Preferably, the treated biomass containing more digestible plant polymers is consumed by an animal. Preferably, the plant biomass is fermented to produce ethanol.

One skilled in the art will realize that within a facility pretreating biomass containing some water with ammonia and perhaps adding more water, heating the mixture, allowing the hot ammonia:water:biomass combination to react for a time, ending the reaction by removing the ammonia from biomass, and separating ammonia from water in the recovery process, a variety of possible ammonia:water:biomass combinations present themselves. Some combinations may prove more technically and/or economically effective than others in producing a highly reactive biomass. The present invention relates to effective treatments of a plant biomass to increase the reactivity of plant structural carbohydrates. The results are novel, unexpected and useful. At the same final conditions (temperature, amount of total water, ammonia and biomass mixed with each other), uniquely effective combinations of ammonia, water and biomass are available. Other combinations giving the same final conditions are much less effective in producing a highly reactive biomass.

For example, Table 2 shows the results of enzymatic hydrolysis of biomass treated with ammonia, water and heat under the same final conditions of 1 kg of ammonia per 1 kg of corn stover biomass (dry weight) and 0.6 kg of water per kg of corn stover biomass (dry weight) at a final reaction temperature of 90° C. These final conditions were chosen to reproduce the optimal pretreatment conditions demonstrated for "conventional" (using anhydrous ammonia) AFEX treatment of corn stover. The first row of results shows the glucose and xylose yields (92.96% and 74.75%, respectively) obtained under these "conventional" AFEX pretreatment conditions. As stated above, it is apparent to one skilled in the art, that different combinations of ammonia, water and biomass will be available, or could readily become available, in a pretreatment facility. The question is: "which combinations of these are most effective in producing a highly reactive pretreated biomass". Experiments 1-15 provide a preliminary answer to this critically important question.

Final glucose yield, and to a lesser extent, xylose yield, following enzymatic hydrolysis are key determinants of process economics for biomass conversion systems. If 90% yield of glucose is somewhat arbitrarily chosen as the target economic yield, then it becomes obvious that only a fraction of all of the possible means for reaching the desired final conditions of 1:1 ammonia to biomass and 0.6:1 water to biomass are in fact effective in achieving this target yield. For example, from Table 2, experiments #6 and #9 differ only in the amount of water that is added to the system via biomass or via ammonium hydroxide, and yet the differences in enzymatic hydrolysis yields are huge, 58% vs. 99%, respectively. These results are unexpected, novel and useful. It is not apparent at all why combining ammonia, water and biomass in different initial proportions but the same final proportions should achieve such different results, but in fact, this is what happens. It is a novel result that has never before been reported, to the inventor's knowledge. Finally, it is an extremely useful result because the operator of the pretreatment facility now has available different routes to achieving an effective pretreatment. Some of these sets of effective conditions may prove much easier or less expensive to implement in an operating pretreatment facility, and hence will be preferred.

One skilled in the art will also recognize that it is necessary to maintain ammonia and water in effective contact with the biomass during the pretreatment process. The present invention also provides means for maintaining ammonia and water in contact with the heated mixture by minimizing or otherwise managing the headspace (vapor phase) of the reactor containing heated biomass, ammonia and water. Various approaches can be envisioned to achieve this objective. Preferably, the ammonia in step (b) is compressed by a mechanical means for reducing the volume of a headspace inside the closed vessel and thereby increasing a fraction of the total ammonia that is in the liquid phase. Preferably, nitrogen or another inert gas under pressure is introduced into a headspace of the vessel in step (b) so as to increase a fraction of the total ammonia that is in the liquid phase. Preferably, particles of an inert solid material are introduced into the vessel so as to increase a fraction of the total ammonia that is in the liquid phase. Preferably, particles of a solid material selected from the group consisting of sand and iron filings are introduced into the vessel so as to increase a fraction of the total ammonia that is in the liquid phase. FIGS. 3 and 4 show that by maintaining nitrogen pressure on the headspace of the reactor, the amount of ammonia required to obtain a desired glucose yield can be reduced. Nitrogen overpressure minimizes the amount of ammonia that evaporates from the biomass and keeps more ammonia in contact with the biomass, thereby increasing treatment effectiveness. This is strong support for the idea that minimizing ammonia in the gas phase will maximize treatment effectiveness. Obviously, other means of minimizing gas phase ammonia are available. These include combining inert solids (e.g., sand or iron filings) or simply connecting the headspace of the reactor with the headspace of a storage vessel containing ammonia and water that provides the same gas phase composition of ammonia and water as is produced under the desired reactor conditions of temperature, ammonia and water levels.

The present invention also includes a method for treating biomass, comprising the following steps: providing biomass in a reaction vessel; providing gaseous ammonia; delivering the gaseous ammonia to the reaction vessel; allowing time for the gaseous ammonia to react with the biomass in the reaction vessel; and removing the biomass from the reaction vessel.

In certain embodiments of the present invention, the temperature in the reaction vessel may be from about 50° C. to about 200° C.; or the temperature in the reaction vessel may be from about 50° C. to about 100° C.; or the temperature in the reaction vessel may increase after delivery of the gaseous ammonia to the reaction vessel.

In other embodiments of the present invention, the gaseous ammonia may be delivered to the reaction vessel at a pressure from about 100 psi to about 1000 psi, from about 200 psi to about 650 psi, or from about 100 psi to about 200 psi.

Further aspects of the inventive method include the gaseous ammonia condensing on the biomass. Additionally, the biomass may include less than about 15% water on a dry weight basis; from about 15% water to about 233% water on a dry weight basis; or the gaseous ammonia reacts with water in the biomass.

In another aspect of the present method, the time for the gaseous ammonia to react with the biomass may be from about 2 hours to about 36 hours, from about 2 hours to about 12 hours, from about 1 minute to about 120 minutes, from about 1 minute to about 20 minutes.

Also, with the present inventive method, the biomass may be uniformly pretreated by the gaseous ammonia; the method may be continuous or semi-batch; and the reaction vessel may be a fixed bed reactor, a fluidized bed reactor, or a semi-fluidized bed reactor.

In some embodiments of the present method, a carrier may be delivered to the reaction vessel, and the carrier may be added to the reaction vessel after the gaseous ammonia gas is delivered to the reaction vessel. The carrier may be combined with the gaseous ammonia, it may be an inert gas, it may be oxidative (e.g., air), and it may be steam. Further, an inert gas and steam may be combined with the gaseous ammonia before the gaseous ammonia is delivered to the reaction vessel.

In a further embodiment, the present method further may include recycling at least a portion of the gaseous ammonia as a gas to be used in the treatment process.

The present invention also includes a method for treating biomass, including: impregnating biomass with ammonia; delivering the biomass to a reaction vessel; providing a gaseous carrier; delivering the gaseous carrier to the reaction vessel; allowing time for the gaseous carrier to react with the biomass in the reaction vessel; and removing the biomass from the reaction vessel.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings and tables, certain embodiment(s) which are presently preferred. It should be understood, however, that the invention is not limited to the precise arrangements and instrumentalities shown.

In FIG. 11, liquid ammonia is added to the reaction vessel for conventional AFEX treatment (I); and for GAP, the ammonia delivery vessel is heated to transform liquid ammonia to its gaseous state (at pressure P1) and the gaseous ammonia is added to the biomass in the reaction vessel (such that the final pressure in the reaction vessel is P2).

FIG. 17A, untreated; FIG. 17B, low-moisture AFEX treated; FIGS. 17C and 17D are different portion and magnification of low moisture AFEX treated samples. Untreated corn stover has a distinctinctive multi-lamellar cell wall compared to the nano-porous AFEX treated cell wall. There is a hint of surface deposits on the outer cell wall layers seen as a wavy, amorphous appearance after AFEX.

DETAILED DESCRIPTION OF THE PREFERRED EMBODIMENTS

Figure 1:
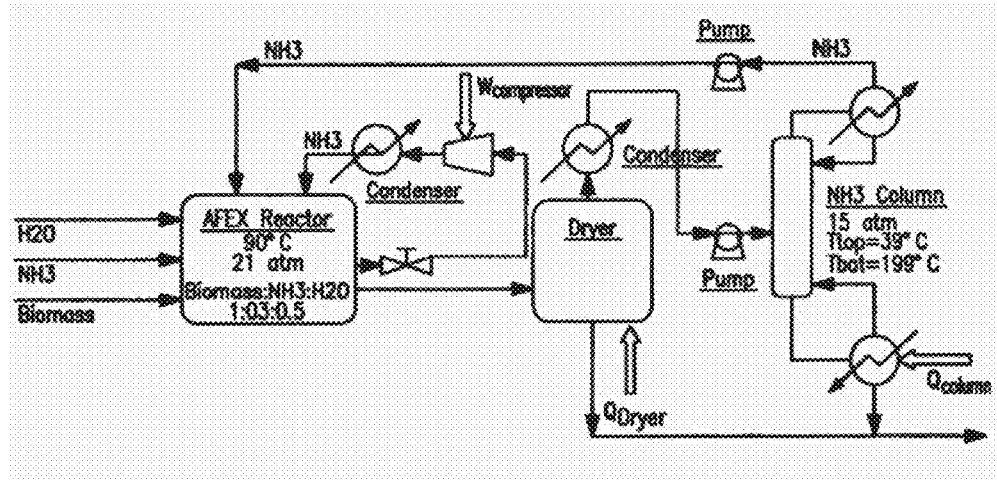
FIG. 1 is a process flow diagram for a prior art AFEX pretreatment with ammonia recovery and recycling.

Before the subject invention is described further, it is to be understood that the invention is not limited to the particular embodiments of the invention described below. It is also to be understood that the terminology employed is for the purpose of describing particular embodiments, and is not intended to be limiting.

All references, patents, publications, articles, databases, and other writings referred to in this application are incorporated herein by reference in their entirety, as if each were specifically and individually incorporated herein by reference. Such patents, publications, articles, databases, and other writings are incorporated for the purpose of describing and disclosing the subject components of the invention that are described in those patents, publications, articles, databases, and other writings which components might be used in connection with the presently described invention. The information provided below is not admitted to be prior art to the present invention, but is provided solely to assist the understanding of the reader.

The details of one or more embodiments of the invention are set forth in the description below. The preferred embodiments of the present invention may be understood more readily by reference to the following detailed description of the specific embodiments and the Examples included hereafter.

Unless defined otherwise, all technical and scientific terms used herein have the meaning commonly understood by one of ordinary skill in the art to which this invention belongs. Although any methods, devices and materials similar or equivalent to those described herein can be used in the practice or testing of the invention, the preferred methods, devices and materials are now described.

In this specification and the appended claims, the singular forms "a," "an" and "the" include plural reference unless the context clearly dictates otherwise.

The term "ammonia" as used herein means a compound of nitrogen and hydrogen with the formula $NH_3$.

The terms "biomass" or "lignocellulosic biomass" as used herein mean an organic material derived lignin and cellulose, such as wood, plants, and organic wastes (e.g., alfalfa, wheat straw, corn stover, wood fibers) that can be turned into fuel. Preferably the materials are comminuted into particles in a longest dimension.

The term "gaseous" as used herein means the state of matter distinguished from the solid and liquid states by density, viscosity and/or expansion.

The term "structural carbohydrates" as used herein means the polysaccharide materials containing monosaccharide moieties available by hydrolysis.

Cellulosic biomass contains large amounts of structural carbohydrates or polysaccharides (cellulose, hemicellulose, and the like) that can provide much less expensive simple sugars for fermentation or non-biological transformation to a variety of products or as improved animal feeds. However, these polysaccharides are difficult to access. The present invention provides pretreatment process using concentrated ammonium hydroxide under pressure to improve the accessibility/digestibility of the polysaccharides from a cellulosic biomass. The present invention preferably uses combinations of anhydrous ammonia and concentrated ammonium hydroxide solutions to obtain results that are not obtained by either dilute ammonium hydroxide or anhydrous ammonia acting alone. This invention also uses various approaches to minimize the amount of ammonia in the gas phase so that the maximum amount of ammonia is always in the liquid phase and is available to react with the biomass, either as ammonium hydroxide or liquid ammonia.

In the present invention, the lignocellulosic material is treated with concentrated ammonium hydroxide in an amount greater than 30% by weight in an ammonium hydroxide solution. The process can be performed in a continuous reactor or a batch reactor as in the Examples.

The biomass contains water which is naturally present. Typically, this natural water represents about 1% to 20% by weight of the biomass. In general, this natural water tends to be bound in the biomass and thus the water which is primarily relied upon is that added with the ammonium hydroxide solution. Water can also be added to the biomass and, if so, then this mixes with the ammonium hydroxide to provide the ammonium hydroxide solution. Up to 50% of the biomass can be added water.

The mass ratio of a lignocellulose biomass to ammonia is preferably 1 to 1. However, the mass ratio can be between 0.3 and 1.2 to 1.0.

The reaction temperature is preferably 90° C. However, the temperature can be between 50° C. and 120° C.

The pressure is preferably between 100 psi and 300 psi (6.9 to 20.7 atm). However pressures between 4 and 50 atm can be used.

Hot ammonium hydroxide/water solutions or hot ammonia/water vapors can be added to ground lignocellulosic biomass in a contained vessel to obtain final mixture temperatures of 50° C. or above, preferably 90° C. A preferred ammonia to dry biomass mass weight ratio was about 0.2 to 1.2. A preferred water to dry biomass mass ratio was about 0.4 to 1.0.

Figure 2:
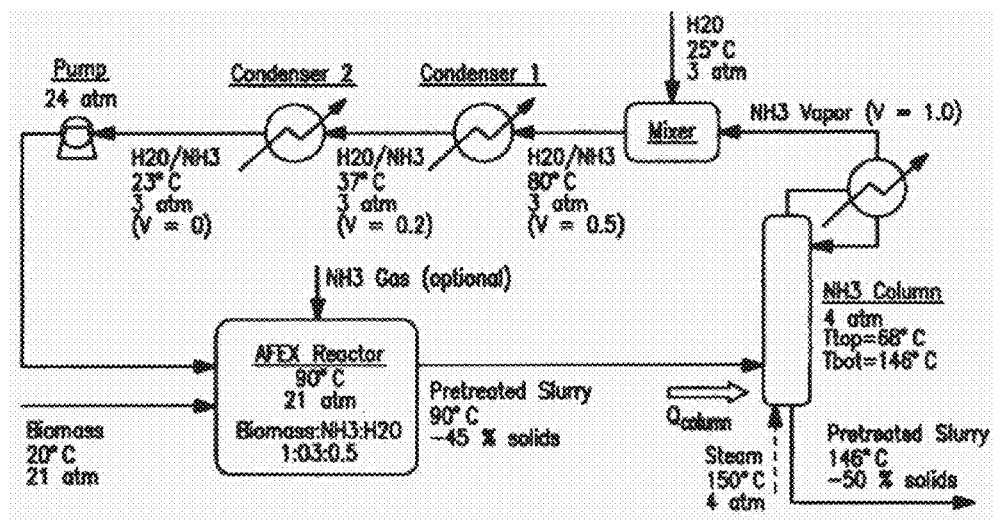
FIG. 2 is a process flow diagram for the present invention for AFEX pretreatment with an efficient ammonia recovery.
Figure 3:
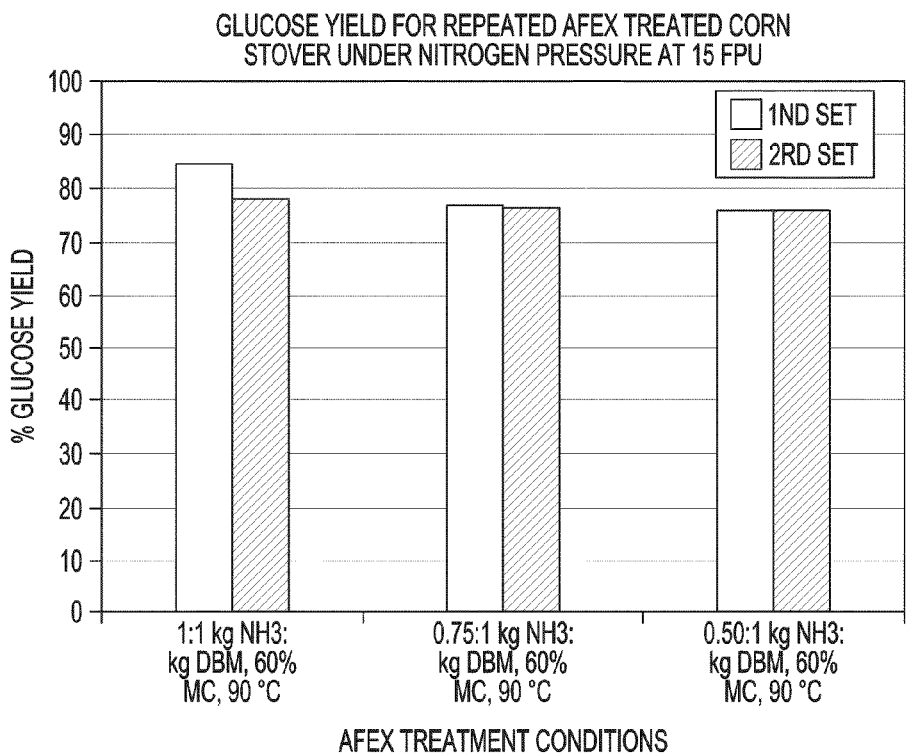
FIGS. 3 and 4 are graphs showing that the two separate AFEX treated corn stover experiments under nitrogen pressure with the same treatment conditions have similar yields.
Figure 4:
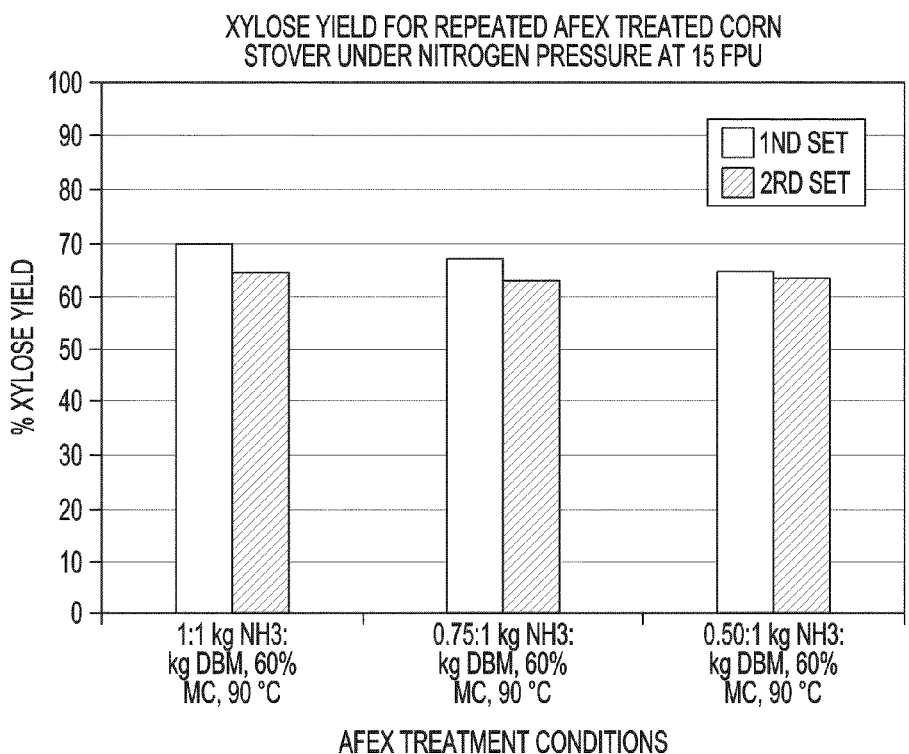
Figure 5:
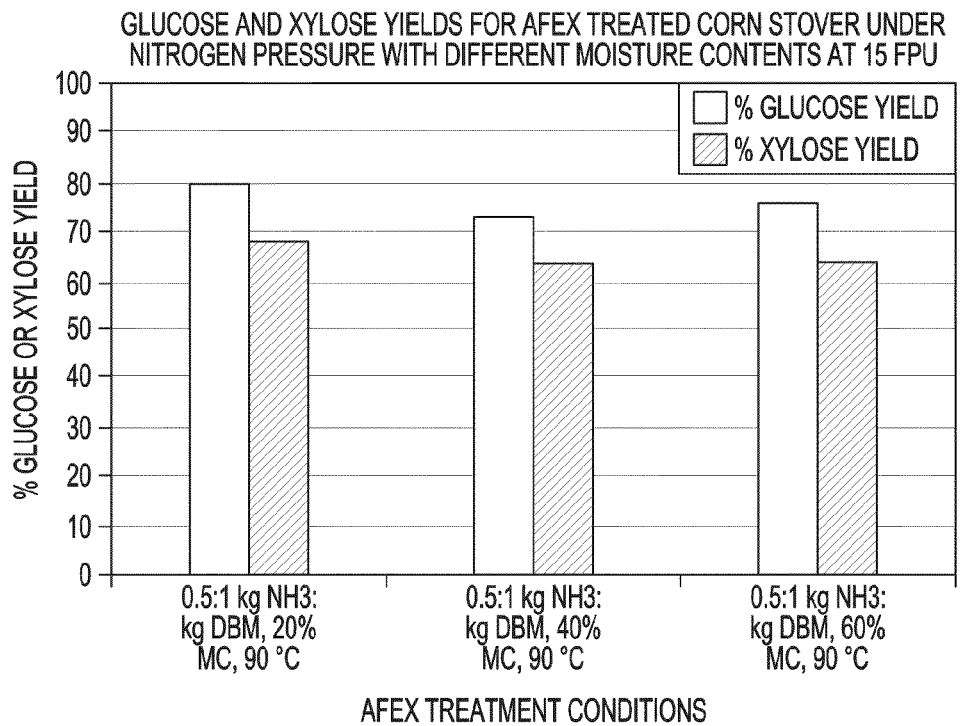
FIG. 5 is a graph showing that while 40% moisture content gives lower yield, 20% biomass moisture content (MC) yields better results a few percent higher than that of 60% MC. The optimal condition has been 60% MC.
Figure 6:
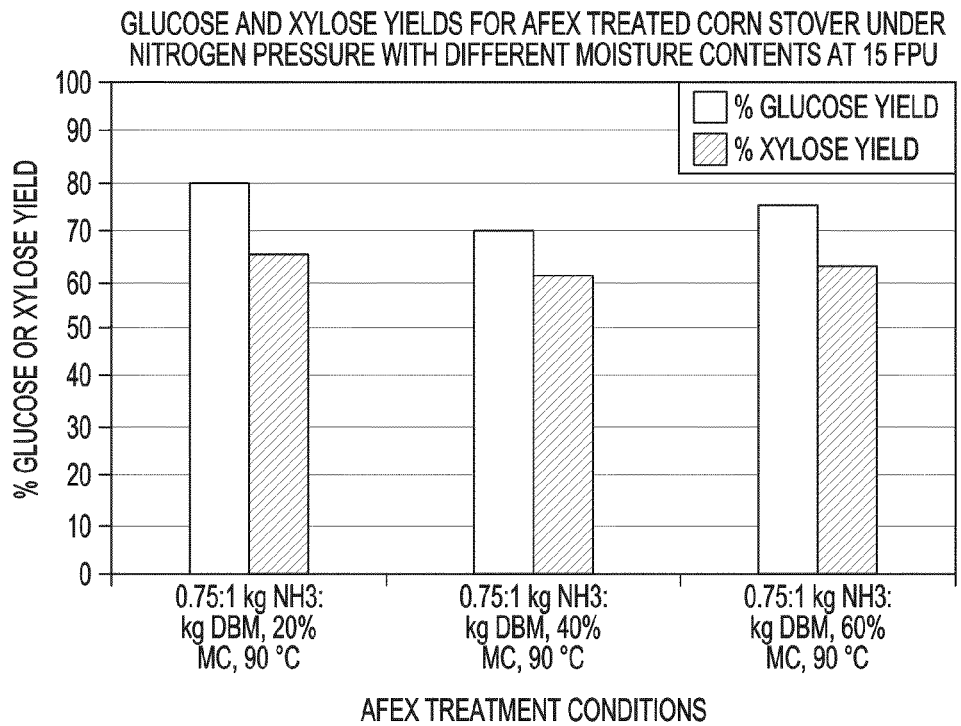
FIG. 6 is a graph showing a similar trend for different sets of experiments with different ammonia loadings. Lower amount of moisture content, i.e., 20% gives a better result.
Figure 7:
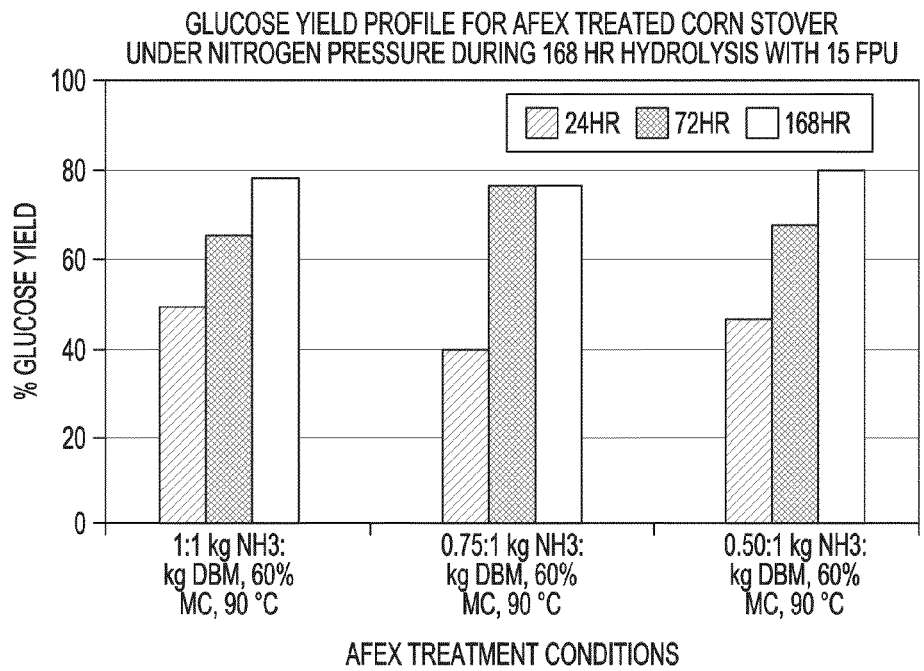
FIGS. 7 and 8 are graphs showing the glucose and xylose profile during 168 hr hydrolysis for different amounts of ammonia loading, respectively. While, both figures show similar hydrolysis rate, 0.75 kg $NH_3$:1 kg DBM is favored.
Figure 8:
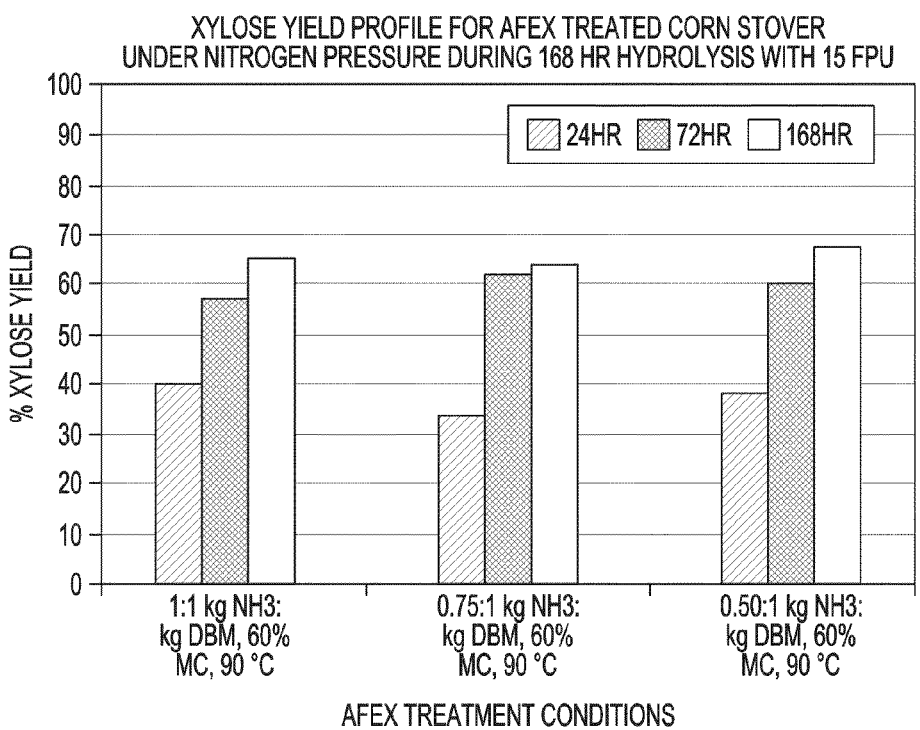
Figure 9:
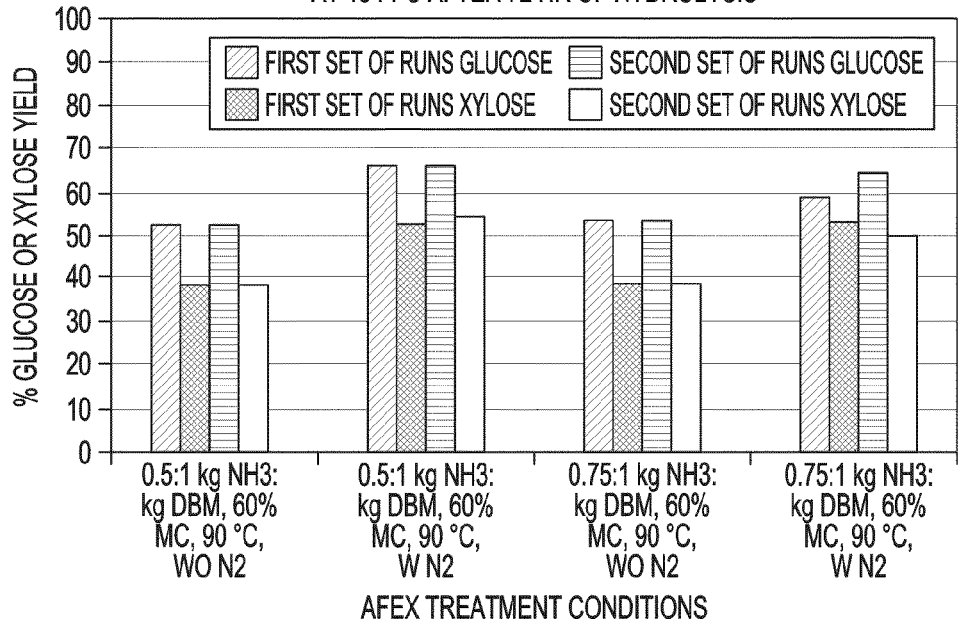
FIG. 9 is a graph showing the overall glucose and xylose yields of two separate sets of AFEX treated corn stover under nitrogen pressure that are repeated. All the runs have yielded very similar results. While higher yield is obtained under nitrogen pressure, a better yield is obtained with 0.5 kg $NH_3$:1 kg DBM, 60% MC under nitrogen pressure.
Figure 10:
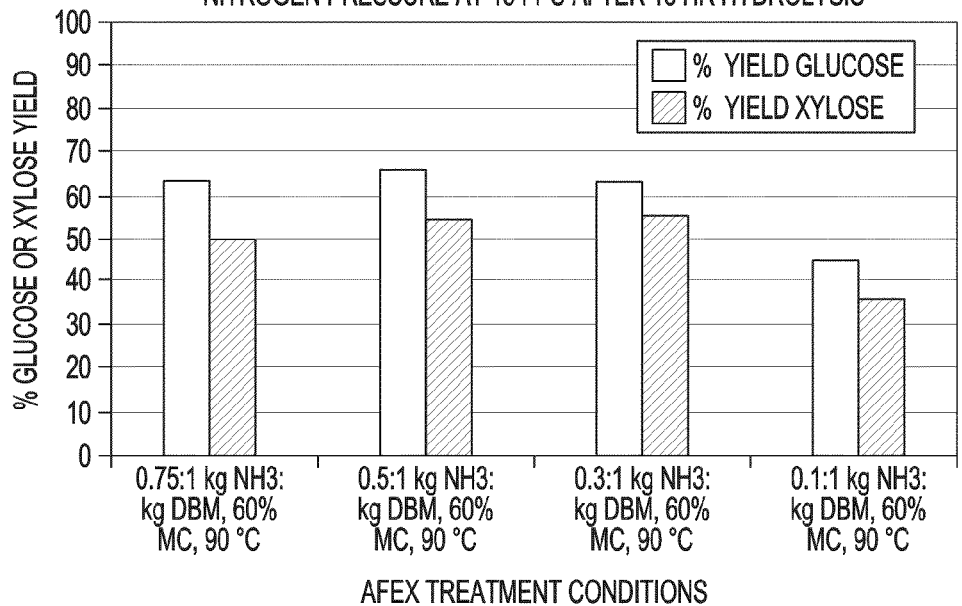
FIG. 10 is a graph showing the yield trend as the kg amount of ammonia per unit kg of dry biomass (DBM) is decreased.

FIG. 2 shows the improved system 100 with AFEX reactor vessel. The slurry is sent directly to the stripping column 104 and condenser in condenser 106 and is sent to mixer 108 for addition of water. High pressure steam is used in the stripping column 104 to remove the ammonia from the slurry. The hot aqueous slurry is removed from the bottom of the stripping column. Condensers 110 and 112 are used to cool the water and ammonia mixture which is recycled into the vessel 102. By comparing FIGS. 1 and 2, it can be seen that the process of FIG. 2 is more efficient.

The inventors also have developed a process identified as "Gaseous Ammonia Pretreatment" (GAP) in which hot ammonia gas (gaseous ammonia) is used to pretreat biomass in a reaction vessel, such as a reactor, or other vessel that is capable of containing the biomass under pressure. For example, with the GAP process, the contents of the reactor may be maintained at pressures ranging from about 0 psi to about 1000 psi, from about 200 psi to about 500 psi, or from about 100 psi to about 200 psi. In one embodiment, water is used to pre-wet the biomass, the hot ammonia gas is delivered to the biomass under pressure. For example, the gaseous ammonia is delivered to the reaction vessel at pressures ranging from about 0 psi to about 1000 psi, from about 200 psi to about 500 psi, or from about 100 psi to about 200 psi. Then, the hot ammonia gas condenses on the biomass and reacts with water. With this method, the desired temperature (from about 50° C. to about 200° C.) is achieved instantaneously due to exothermic reaction between water and ammonia. The formation of ammonium hydroxide takes place rapidly wherever water is associated with the biomass. During this process, the biomass is uniformly pretreated by the ammonia (i.e., the majority of the biomass receives about the same pretreatment) and requires short pretreatment time (e.g., from about 1 to about 120 min, or from about 1 to about 20 minutes). This short pretreatment time also helps reduce formation of potentially inhibitory degradation products that might negatively influence downstream biological processing. In some embodiments of the present invention, longer pretreatment times can be used, e.g., from about 2 to about 36 hours, or from about 2 to about 12 hours. Further, with this method, there is no expansive release of pressure at the end of the pretreatment, allowing significant energy savings during recycling of the ammonia.

The process of the present invention can be easily adapted to a continuous method using a stream of (a) recycled ammonia gas, (b) a mixture of recycled ammonia gas and steam, (c) recycled ammonia gas combined with an inert or other carrier gas, or (d) a recycled ammonia/steam gas mixture combined with an inert/carrier gas in any of a fluidized bed reactor, a semi-fluidized, bed reactor, or a fixed bed reactor. It is expected that only a small portion of ammonia (about 0.5 to about 3%, w/w of ammonia/biomass) will be reacted during the present process (due to reaction of ammonia with various cell wall components) and the remaining ammonia (i.e., from about 50% to about 99.5%, from about 75% to about 99.5%, or from about 97% to about 99.5%, w/w of ammonia/biomass) can be recycled in its gaseous state.

In one embodiment, hot ammonia gas is used to treat pre-wetted biomass (from about 15% to about 233% moisture, e.g. water content, dry weight basis) in a reactor with continuous recycling of ammonia-water gaseous mixture (e.g., gaseous ammonia/steam). In another embodiment, a hot ammonia-water gas mixture is used to pretreat either pre-wetted or dry biomass (less than about 15% moisture, dry weight basis, "dwb"), which ammonia-water gas mixture is continuously fed to the reactor and ammonia-water gas mixture is recycled back to the reactor. In a further embodiment, hot ammonia gas is fed to a reactor in combination with a hot inert/carrier gas (e.g., nitrogen, air) to pretreat pre-wetted (from about 15% to about 233% moisture, dry weight basis) or dry biomass (about 15% moisture or less, dwb), which hot ammonia gas is continuously fed to the reactor with recycle of the ammonia-water-inert gas mixture. Alternatively, an oxidative gas, such as air or oxygen, can be combined with the ammonia gas. In another embodiment, a hot ammonia-water gas mixture is fed to a reactor in combination with a hot inert/carrier gas (e.g., steam, nitrogen, air) to pretreat pre-wetted (from about 15% moisture to about 233% moisture, dwb) or dry biomass (about 15% moisture or less, dwb), which hot ammonia-steam gas mixture is continuously fed to the reactor with recycling of the ammonia-steam-inert gas mixture. As provided by this invention, the recycling step is expected to reduce the amount of ammonia necessary to pretreat the biomass. As only a small amount of the gaseous ammonia reacts with the biomass (from about 0.5 to about 3%, w/w of ammonia/biomass), it is expected that a hot inert carrier gas would provide a suitable heat and mass transfer medium replacing expensive ammonia used in current methods (AFEX).

Further, in another embodiment, the carrier gas [either oxidative (e.g., oxygen or air) or non-oxidative (e.g., nitrogen or steam)] are used either combined with gaseous ammonia during the pretreatment process or after the pretreatment process (to remove residual ammonia from the biomass).

Figure 12:
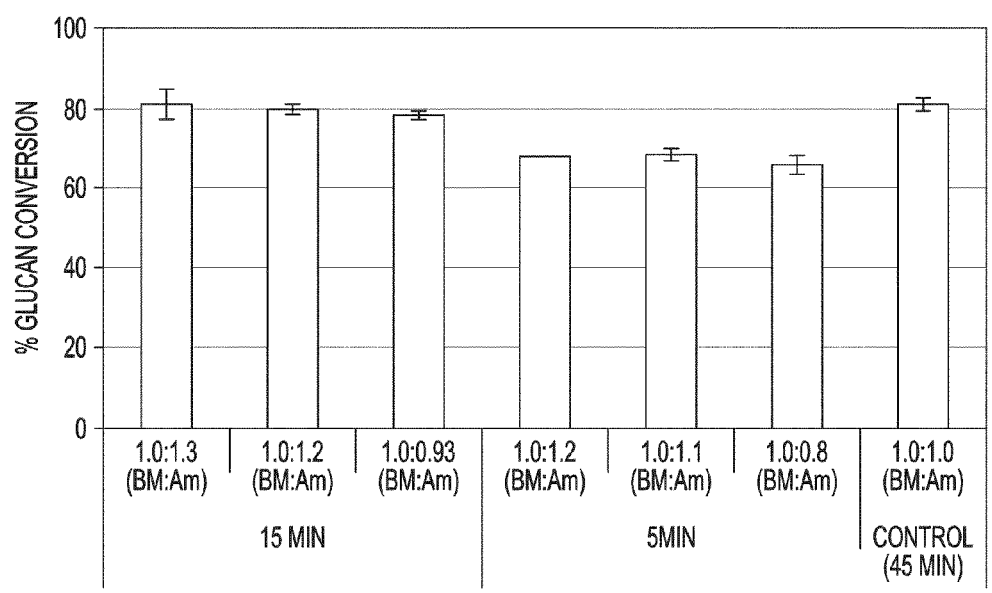
FIG. 12 shows enzymatic hydrolysis based glucose yield from corn stover pretreated using AFEX (control) and GAP process at two different residence times as a function of ammonia loading.

With the present inventive method, effective biomass to ammonia loading is from about 1:0.01 to about 1:5, from about 1:0.2 to about 1:2, or from about 1:0.2 to about 1:1. Further, with the present inventive method, glucan conversion rates are the same, or higher (by about 10-15%) than conversion rates for conventional AFEX. For example, as shown in FIG. 12, a 15 minute reaction time with GAP achieves a relatively equivalent conversion rate as a 45 minute reaction time with AFEX. With a 30 minute reaction time with GAP, however, it is expected that the glucan conversion would be increased 10-15% as compared to the AFEX process. Generally, such conversion rates are dependent on other factors, such as, the particular cellulases and hemicellulases, the type and combination of enzymes, and the amount of enzymes used in the enzymatic hydrolysis.

The present invention also includes impregnating biomass with liquid or gaseous ammonia and water (using concentrated/dilute ammonium hydroxide) to achieve lower ammonia loadings (from about 0.01 to about 0.3 kg ammonia per kg biomass) and then feeding the biomass to the reactor continuously where it is pretreated using a hot inert carrier gas (containing little or no ammonia). In one embodiment, this process is performed in a fixed biomass bed reactor with hot ammonia/steam/inert/carrier gas mixtures being purged through the reactor. The gas stream is continuously recycled using compressors and heaters to re-circulate through the fixed biomass bed reactor.

Figure 11:
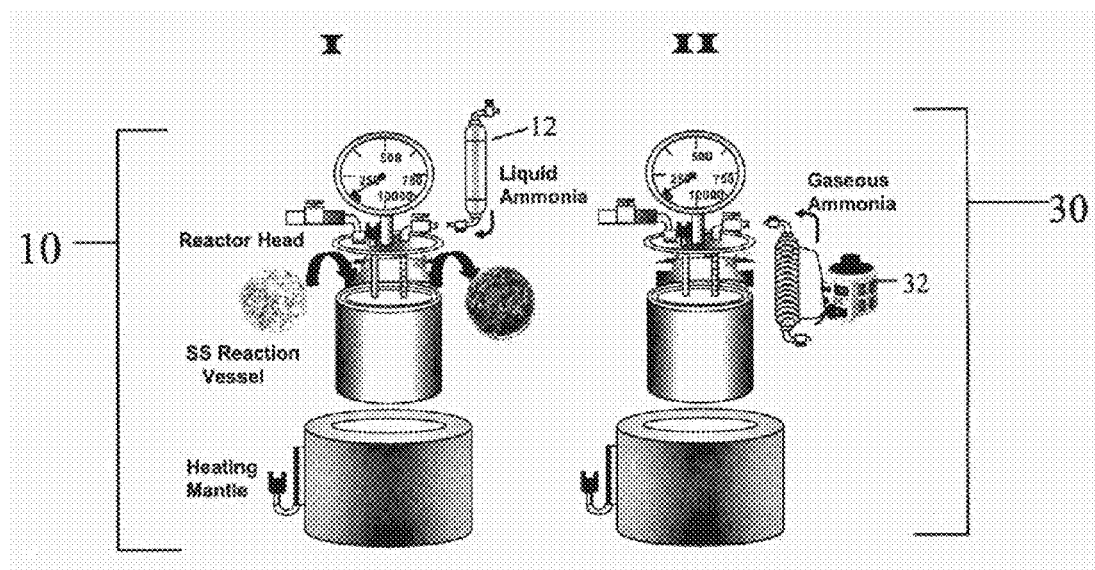
FIG. 11 shows a comparison of conventional AFEX process (I) and gaseous ammonia pretreatment (II).

FIG. 11 shows a schematic sketch of a comparison of (I) a conventional AFEX apparatus 10 and an apparatus 30 for performing the inventive GAP process (II). Unlike AFEX, where liquid ammonia (delivery vessel pressure at 100-200 psi) is fed to a reactor through the bottom valve of an ammonia delivery vessel 12, in GAP, ammonia in the delivery vessel 32 is pre-heated (to delivery vessel) and fed from the top valve of the delivery vessel 32. Unlike conventional AFEX, this configuration permits the hot ammonia gas to condense on the biomass in GAP, thereby causing a fast (e.g., instantaneous) rise in temperature in the reactor. With the AFEX process, it typically takes 15-45 minutes to reach the desired pretreatment temperature in the reactor (e.g., 100° C.), after which the temperature is maintained for another 5-45 min. With the AFEX process, typical time pretreating biomass ranges between 20-90 min. In contrast, with GAP (depending on the temperature and pressure P1 of the hot ammonia gas fed to the reactor), one can rapidly reach the desired pretreatment temperature in the reactor (e.g. from about 50° C. to about 200° C., or from about 50° C. to about 100° C.), with a total residence time between about 1 minute and about 120 minutes.

The inventors also have conceived of novel reactor configurations to continuously feed a column based reactor with hot ammonia and/or inert carrier gas mixtures that are recycled and re-fed to the reactor in its gaseous state (without compression of gaseous ammonia to liquid ammonia or ammonium hydroxide mixtures).

Figure 15:
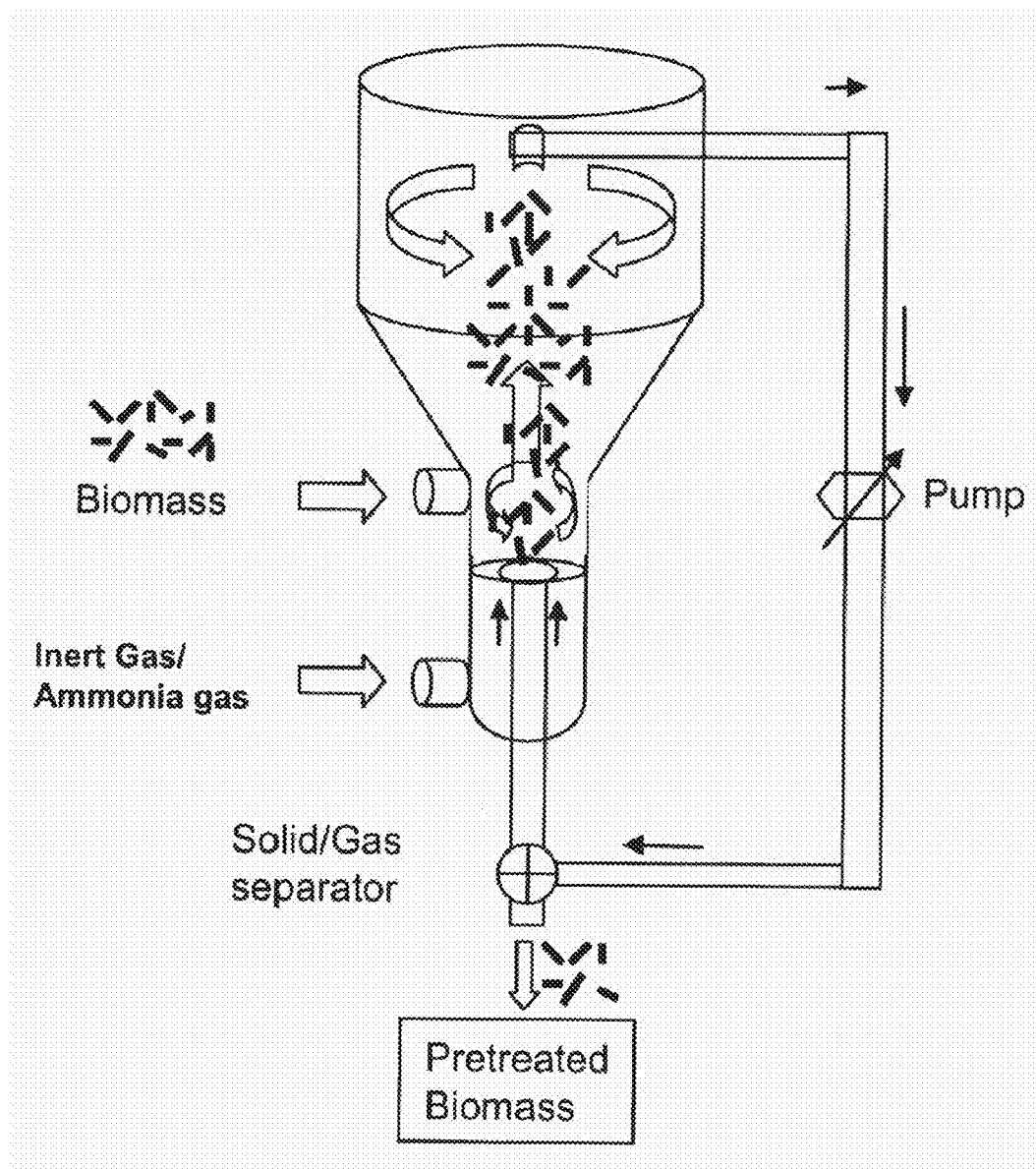
FIG. 15 shows the potential application of fluidization during GAP process using gaseous ammonia with or without suitable hot carrier gases.

There are several reactor variations that may be used to conduct the GAP process. For example, a semi-batch or continuous reactor with fluidized or semi-fluidized biomass fed continuously into a reactor where the biomass is contacted with hot ammonia and/or inert-carrier gas. In one embodiment, the hot gas may be recovered and recycled. In another embodiment, a batch reactor with a fixed bed of biomass is continuously purged with hot ammonia and/or inert-carrier gas; and the hot gas may be recovered and recycled back into the reactor (see, FIG. 15). FIG. 15 illustrates one potential process flow schematic for how GAP may be carried out by fluidizing the biomass using gaseous ammonia and other carrier gases. Some of the advantages of fluidized-based treatment are the uniform pretreatment conditions and ease in scaling up as a continuous process along with ease in recycling and reusing hot gaseous ammonia.

With the present GAP biomass pretreatment process, the pretreatment is as homogeneous as possible; and there are negligible mass transfer issues, negligible heat transfer issues, low residence times, low ammonia/water usage, and complex ammonia-water separation procedures are avoided.

Further, as shown in Table 1, the GAP process using a fluidization method will have several advantages as compared to AFEX.

TABLE 1

| AFEX | Fluidized GAP Process |
| --- | --- |
| Liquid bulk phase reaction | Gas bulk phase reaction |
| Mixing with impellers (non-uniform mixing) | Mixing done by fluidizing gas (uniform mixing) |
| Use of water (40-100%) (difficult to separate ammonia after pretreatment) | Minimize use of water (<10%) |

TABLE 1-continued

| AFEX | Fluidized GAP Process |
| --- | --- |
| Preheated liquid ammonia (expensive to recover & liquefy) | Preheated gaseous ammonia (recycle with no liquefaction) |
| Poor mixing (more ammonia-water needed) | Effective mixing (more efficient usage of ammonia-water) |
| Higher residence time (16-46 min) | Lower residence time (1-15 min) |
| Hot spots due to non-uniform heating | Homogeneous heating and better control over reaction kinetics |

Figure 18A:
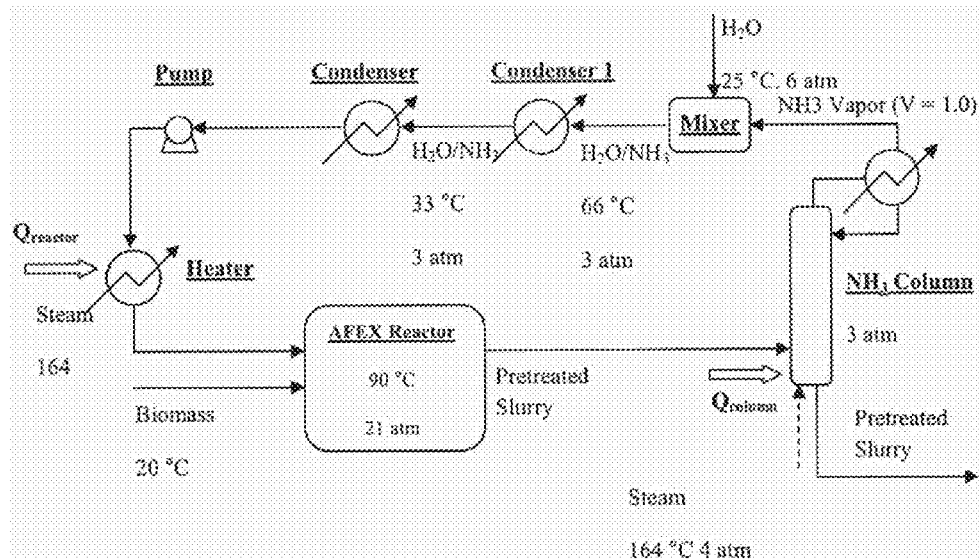
FIG. 18 shows ammonia recovery system and process flow diagram using conventional AFEX (FIG. 18A) and GAP (FIG. 18B) processes.
Figure 18B:
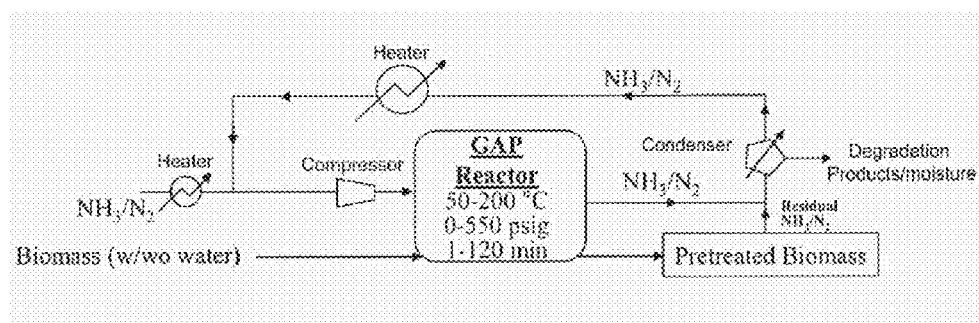

FIGS. 18A and 18B show a biomass and ammonia/inert gas flow diagram of the recovery process for each of the AFEX and GAP processes, respectively. With respect to the GAP process shown in FIG. 18B, the process comprises a GAP Reactor where biomass is fed, with or without water, followed by injecting into the GAP reactor hot ammonia gas ($NH_3$)/nitrogen ($N_2$) using a heater and compressor. Most of the hot ammonia gas and nitrogen are recovered after the GAP process and preheated for the subsequent use in the pretreatment process. The residual ammonia/nitrogen present in the pretreated biomass is recovered using a condenser and used for subsequent pretreatment process. The biomass volatiles (degradation products) and moisture along with the residual ammonia is separated from the ammonia recycle stream.

As described herein, there are several pretreatment conditions (temperature of the gaseous ammonia before treatment, pressure P1 of the ammonia before delivery, pressure P2 of the ammonia after delivery, reaction time in the GAP reactor, water content of the biomass, and ammonia loading) that can impact the GAP process. See, various ranges shown in FIG. 18B.

Moreover, the pretreatment conditions are interrelated, i.e., altering one condition may affect another condition. For example, reaction time is dependent on temperature and ammonia pressure. The higher the pressure and temperature of the gaseous ammonia that is delivered to the GAP reactor, the lower the reaction time in the reactor (and the pressure P2 in the reactor would be high as well). Conversely, the lower the pressure P1 and temperature of the gaseous ammonia delivered to the reactor, the longer the reaction time in the reactor (and the pressure would be lower in the reactor as well). Also, the diffusion rate of ammonia through the biomass particle is larger with increase in pressure, which means that the reactant can access the reactive bonds much quicker and reduce the total reaction time. In theory, if gaseous ammonia pressure is doubled, the reaction time should decrease by nearly half, since most reactions in the biomass are pseudo-first order. Set-point temperature can also be achieved more quickly with an increase in pressure, since hot gaseous ammonia also has the task to carry heat through the bulk phase to the interior of the biomass, where reactions are happening. For reaction temperatures close to room temperature (i.e., 25-40° C.) reaction times can be extended up to 24 hours (depending on ammonia loading) for achieving close to 90% conversion, while at 100° C., the total residence time can decrease down to 15 minutes (depending on ammonia loading). In addition to gaseous ammonia pressure and temperature, particle size of the biomass can also affect the reaction time. The smaller the particle size, the faster set-point temperature and pressure in the interior of the particle are achieved, which means that complete conversion should be achieved faster. Finally, the pressure P2 in the reactor can be lowered by decreasing the ammonia fed in to the reactor or by increasing the moisture content of the biomass.

Further, based on varying pretreatment conditions, the inventors found that adding water along with ammonia during the pretreatment process results in two competing reactions; namely, hydrolysis (involving the hydroxyl ion) and ammonolysis (involving the ammonia). The degradation products formed due to hydroxyl ions are mostly acids and are found to be potent inhibitors to microbes in downstream fermentation processes. On the other hand, the ammoniation reaction results in the formation of amides which are found to be significantly less inhibitory to the microbes (unpublished data from Ming W. Lau and Bruce E. Dale). In a typical AFEX process, about 0.5-2 kg water per kg of biomass is used. Because ammonia is soluble in water, it is expensive to distill out ammonia from water after the pretreatment in order to be reused in a continuous biorefinery process.

Figure 16:
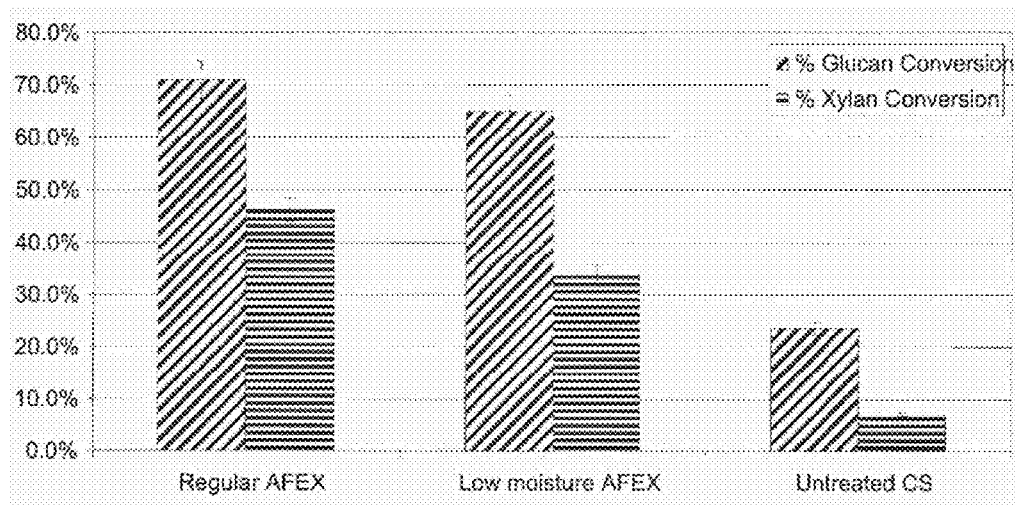
FIG. 16 shows glucose yield for untreated, high moisture (60%, dwb) and low moisture (5%, dwb) AFEX treated corn stover.

Using the GAP process, the inventors expect that biomass containing from about 5 to about 15% moisture, dwb (the expected moisture content of field dried biomass without external water supplementation during pretreatment) can be pretreated with hot ammonia gas and the percent glucan conversion is similar to that obtained from high moisture (15% or more, dwb) ammonia pretreatment as shown in FIG. 16.

The GAP process could be used in a lignocellulosic biorefinery. Specifically, a modern biorefinery will utilize about 2000 tons/day of lignocellulosic biomass for producing biofuels and biochemicals. At present pretreatment, processing costs and green house gas (GHG) emissions are considered as few of the bottle necks for such a biorefinery. Using the GAP process, both pretreatment cost and GHG emissions could be reduced and the technology will be more feasible for the biorefinery. See, e.g., Table 4 hereinbelow.

The GAP process could be used in the edible oilseed and oilcake industry. Oilseeds are typically extracted in two stages: (i) mechanical expeller/press extraction for reducing oil content to 20-25% (w/w), followed by (ii) hexane extraction to remove residual oil (16). The extracted oilcake is then toasted (or desolventized) by steam stripping/cooking to remove residual solvent and pre-conditioned (i.e., to detoxify anti-nutritional components in the oilseed) for animal consumption and/or protein extraction. The pre-conditioning process is generally dependent on the type of oilseed, but typically requires cooking the biomass (at suitable moisture content) with steam at 90-110° C. for a period of 15-30 min. The GAP process could be used along with a typical steam toasting process in order to pretreat the biomass prior to subsequent biological processing for producing biofuels and chemicals (e.g., ethanol and biodiesel). The fiber portion of the oilcake could be fermented to ethanol and reacted with the oil extracted from the oilseed to produce biodiesel as well.

One of the major advantages of the AFEX and GAP processes is that, unlike other thermochemical treatments (e.g., dilute acid, organosolv), the temperature severity of pretreatment is fairly low (e.g., 50-150° C. for GAP vs. 150-220° C. for acidic treatments). Lower temperatures help reduce protein degradation and improve digestibility of important amino acids, like lysine. Ammoniation based treatments are currently employed in the detoxification of oilseeds like groundnuts to remove toxic aflatoxins (17). The inventors have conducted pretreatment of extracted oilseed cakes using a typical AFEX process and hydrolyzed with cellulase enzymes. The AFEX process was found to significantly enhance the rate and yield of maximum achievable sugars compared to the untreated sample (data not shown). The GAP or AFEX pretreatment processes could be used to pretreat oilseed cakes for biomass conversion applications. See, e.g., Balan, V., et al., 2009. *Journal of the American Oil Chemists' Society*, 86, 157-165.

The GAP process could be used for protein extraction as animal feed. In the Pro-Xan process (18) proteins are extracted from alfalfa through hammer milling to disrupt cell walls followed by juice extraction from screw press and steam injection to coagulate proteins. Finally, solubles are added to press cake and sold as animal feed. In this process, ammonia is used to kill different microbes and to raise the pH (which help extract protein). In this process, GAP could again be used at a slightly elevated temperature (instead of room temperature), i.e., from about 30° C. to about 50-100° C. Such conditions will not only further improve the protein extraction, but also pretreat the biomass, which could be used in a biorefinery to make biofuels and biochemicals.

The inventors have performed both in vivo and in vitro digestions studies of AFEX treated biomass and found them to be highly digestible. Based on the digestions studies, animals need much less expensive feeds to achieve adequate growth and milk production if these feeds are pretreated by ammonia.

Having now generally described the invention, the same will be more readily understood through reference to the following Examples, which are provided by way of illustration, and are not intended to be limiting of the present invention, unless specified.

EXAMPLES

Examples 1 to 20

Conversion of Corn Stover to Glucose and Xylose Following Treatment with Ammonia and Water A 300 ml pressure vessel 102 was first filled with a given mass of corn stover wetted to the desired moisture level, as indicated in Table 2, and the vessel 102 was sealed. Thereafter, a concentrated ammonium hydroxide mixture was prepared by mixing the right proportions of anhydrous ammonia and water in another pressure vessel. This mixture was added to the corn stover in the 300 ml reactor vessel 102 to achieve the desired final level of ammonia and water. In this case, the target was 1 kg of ammonia per kg and dry biomass and 0.6 kg of water per kg of dry biomass. The mixture of ammonia, water and biomass was then heated to 90° C., held at that temperature for 5 minutes, and the pressure rapidly released.

The resulting solid was hydrolyzed to mixtures of monosaccharides containing, for example, glucose, xylose and arabinose.

The results of the present invention are shown in Table 2 and Examples 2 to 15.

TABLE 2

Glucose and Xylose yields of ammonia treated corn stover after 168 hr (7 days) for hydrolysis with a cellulase enzyme. Different ammonia concentrations were used. All runs are at 1 kg $NH_3$:1 Kg dry stover (BM), 90° C., reactor temperature, 0.6 kg water/kg dry stover (except for the last 4 experiments 17 to 20) and 5 min residence time. 15 FPU cellulase enzyme/gram glucan in BM.

| Expt. # | Kg $NH_3$/kg water in ammonium hydroxide | Ammonia distribution | Water distribution | % Glucose yield | % Xylose yield | Re-peats |
|---|---|---|---|---|---|---|
| 1(a) | 1 | All $NH_3$ | All in BM | 92.96 | 74.25 | 2 |
| 2 | 0.5 | ¾ $NH_3$ and ¼ $NH_4OH$ | ½ in $NH_4OH$ ½ in BM | 92.20 | 78.85 | 2 |
| 3 | 0.5 | ¾ $NH_3$ and ¼ $NH_4OH$ | All in $NH_4OH$ | 79.88 | 64.90 | 2 |
| 4 | 0.41 | ⅔ $NH_3$ and ⅓ $NH_4OH$ | All in $NH_4OH$ | 86.60 | 70.54 | 1 |
| 5 | 0.58 | ⅔ $NH_3$ and ⅓ $NH_4OH$ | ½ in $NH_4OH$ ½ in BM | 78.23 | 65.83 | 1 |
| 6 | 0.5 | ½ $NH_3$ and ½ $NH_4OH$ | All in $NH_4OH$ | 57.65 | 47.85 | 1 |
| 7 | 0.8 | ½ $NH_3$ and ½ $NH_4OH$ | ¾ in NH4OH and ¼ in BM | 85.50 | 70.37 | 1 |
| 8 | 0.66 | ½ $NH_3$ and ½ $NH_4OH$ | ½ in $NH_4OH$ ½ in BM | 97.78 | 81.98 | 2 |
| 9 | 0.79 | ½ $NH_3$ and ½ $NH_4OH$ | ¾ in BM and ¼ in $NH_4OH$ | 98.54 | 78.70 | 2 |
| 10 | 0.38 | ⅓ $NH_3$ and ⅔ $NH_4OH$ | All in $NH_4OH$ | 74.52 | 56.47 | 1 |
| 11 | 0.73 | ⅓ $NH_3$ and ⅔ $NH_4OH$ | ½ in $NH_4OH$ ½ in BM | 81.51 | 69.66 | 1 |
| 12 | 0.66 | All $NH_4OH$ | All in $NH_4OH$ | 71.00 | 57.00 | 2 |
| 13 | 0.75 | All $NH_4OH$ | ½ in $NH_4OH$ ½ in BM | 96.78 | 79.00 | 3 |
| 14 | 0.88 | All $NH_4OH$ | ¾ in $NH_4OH$ and ¼ in BM | 97.11 | 79.00 | 2 |
| 15 | 0.72 | All $NH_4OH$ | ¼ in $NH_4OH$ and ¾ in BM | 88.31 | 75.37 | 2 |
| 16(b) | 0.3 | All $NH_4OH$ | 2.3 g water per g BM | 83.58 | 68.18 | 1 |
| 17(b) | 0.15 | All $NH_4OH$ | 5.6 g water per g BM | 70.50 | 42.46 | 1 |
| 18(b) | 0.1 | All $NH_4OH$ | 9 g water per g BM | 64.85 | 49.31 | 1 |
| 19(b) | 0.05 | All $NH_4OH$ | 19 g water per g BM | 51.26 | 39.32 | 1 |
| 20(c) | Control | No ammonia | Not applicable | 29.5 | 17.5 | 2 |

Note:
Pressures range from about 100 psi to about 300 psi except for Expt. 16-19, which are at atmospheric pressure (a) Comparative Example 1 shows the AFEX process described in U.S. Pat. Nos. 4,600,590 and 5,037,663 to Dale, exemplified by FIG. 1. Comparative Examples 16 to 19 (b) show the results at atmospheric pressure with ammonium hydroxide. Example 20 (c) shows the process without ammonia.

Table 2 shows the results for the conversion of corn stover to glucose and xylose following treatment with ammonia and water. The total amount of water, ammonia and biomass and the system temperature is the same in all cases. The biomass was treated with 1 kg of ammonia per 1 kg dry corn stover biomass (the untreated stover has a moisture content of about 15% dry basis). The experiments were run at 90° C. with a five minute holding time at that temperature. The treated material of Example 1 was hydrolyzed with 15 filter paper units of cellulose per gram of cellulose in the stover. From the point of view of the final conditions to which the stover was subjected, these conditions are identical. However, the way in which these final conditions were reached was varied significantly and novel, surprising results were obtained.

Columns 3 and 4 of the Table show how this was done. For example, the column entitled "Ammonia Distribution" shows whether the ammonia (as $NH_3$) was added as anhydrous ammonia or as ammonium hydroxide (ammonia in water). For example, "all $NH_3$" means that all of the ammonia was added to the biomass as anhydrous liquid ammonia as in Example 1 directly from the pressure tank. "ALL $NH_4OH$" means all of the ammonia was added as aqueous ammonium hydroxide.

The fourth column ("Water Distribution") shows whether the water was added to the stover directly or added as part of the ammonium hydroxide. In the first row for Experiment 1a ("conventional AFEX"), "all NH$_3$" and "All of the water in BM" means that all the ammonia was added as anhydrous and all of the water was in the biomass, as in Example 1. The last set of rows is for "All NH$_4$OH" meaning that all of the ammonia was added as ammonium hydroxide and the water was added either to the stover or with the ammonium hydroxide. These rows (Experiments 16-19) represent essentially ambient pressure treatments of biomass by ammonia, not the concentrated ammonia systems at higher than ambient pressure of Experiments 1-15 above.

Thus, depending on how the ammonia and water are added, very different results are obtained. Eighty-five percent (85%) conversion of cellulose to glucose is used as the minimum for a cost competitive process. Using that criterion, the final column shows the % yield after 168 hours of hydrolysis for both glucose (G) and xylose (X). In no case, when all of the water was added as ammonium hydroxide (comparatively more dilute ammonium hydroxide) is the 85% criterion achieved.

The specific features of the process of the present invention that make it more advantageous than prior art methods are as follows: (1) it does not degrade any biomass carbohydrates so that yield is not compromised due to the pretreatment; (2) high overall yields of glucose (nearly 100% of theoretical) and 85% of theoretical yields of xylose, are obtained; (3) low application rates of otherwise expensive hydrolytic enzymes are needed to obtain these yields; (4) residual ammonia can serve as a nitrogen source for subsequent fermentations or animal feeding operations; (5) treated biomass and polysaccharides can be fed at very high solids levels to subsequent process operations, thereby increasing the concentration of all products and reducing the expense of producing other chemicals from the polysaccharides; (6) using different ammonia and ammonium hydroxide combinations, in combination with different water levels in the biomass, fits well into recovery operations for the ammonia and gives the plant operator additional flexibility to minimize costs and maximize treatment effectiveness; and (7) managing the reactor headspace to minimize ammonia evaporation into the gas phase further improves process economics by minimizing the amount of ammonia required to achieve an effective treatment.

Markets that can use this invention include: (1) the U.S. chemical industry which is beginning to move away from petroleum as a source of chemical feedstocks and is interested in inexpensive monosaccharides as platform chemicals for new, sustainable processes; (2) the fermentation industry, especially the fuel ethanol production industry which is also interested in inexpensive sugars from plant biomass; and (3) the animal feed industry which is strongly affected by the cost of available carbohydrates/calories for making animal feeds of various kinds.

The following Example 16 describes two (2) design features that reduce process energy requirements relative to existing designs of ammonia recovery for AFEX pretreatment: (1) steam stripping of pretreated material; and (2) water quench condensation of ammonia vapor. FIG. 2 presents a process flow sheet of these features in the context of the broader AFEX pretreatment design.

Steam Stripping of Pretreated Material

After the AFEX pretreatment is complete, the pretreated material is flashed to a lower pressure, as in the existing design. Unlike the existing design; however, the present invention uses steam-stripping of the resulting pretreated solids to recover residual ammonia. This feature enables the elimination of energy intensive solids drying that is used in the design of FIG. 1. The processing equipment can be similar to that used for direct steam drying of solids for which there are an increasing number of commercial examples (Kudra, T., A. S. Mujumdar, 2002. Advanced Drying Technologies, New York, N.Y.: Marcel Dekker, Inc.; Pronyk, C., S. Cenkowski, 2003. "Superheating Steam Drying Technologies," ASAE Meeting Presentation, Paper Number RRV03-0014.).

Water Quench Condensation of Ammonia Vapor

Ammonia vapor coming from the ammonia recovery steam stripping column is combined with ammonia vapor arising from the post-AFEX flash operation and condensed by first adding water in the mixer and then indirectly cooling the aqueous solution in two steps, first with cooling water, and then with chilled water. The condensed aqueous mixture is then pressurized via liquid pumping and recycled to the AFEX reactor. These steps eliminate the need for ammonia vapor compression that is used in the design of FIG. 1.

Based on Aspen Plus (a commercially available modeling software) process simulations of the process of FIGS. 1 and 2, the present invention requires significantly less process energy relative to the existing design, as indicated in Table 3. Furthermore, it is anticipated that the invention will result in lower processing costs as well.

Table 3:

TABLE 3

Comparison of process energy requirements: proposed versus existing design for AFEX pretreatment with ammonia recovery.[1,2]

| Energy Flow | FIG. 1 Design Required Energy (% feedstock LHV) | FIG. 2 Design Required Energy (% feedstock LHV) |
|---|---|---|
| Steam to dryer | 7.73% | — |
| Steam to NH3 column | 2.87% | 3.82% |
| Power to compressor | 0.02% | — |
| Power to chilled water unit | — | 0.14% |
| TOTAL | 10.62% | 3.96% |

[1] Energy necessary to achieve AFEX reaction temperature is met entirely by heat of mixing between ammonia and water in the reactor.
[2] Both designs use the same ammonia and water loadings: 0.3 g NH$_3$/g biomass; 0.5 g H$_2$O/g biomass.

These steps are in general:

1. Add hot ammonium hydroxide/water solutions or hot ammonia/water vapors to ground lignocellulosic biomass in contained environments to obtain final mixture temperatures of 50° C.

2. Obtain intermediate ammonia to dry biomass mass ratio is about 0.2 to 1.0 while water to dry biomass mass ratio is about 0.4 to 1.0.

3. Allow sufficient time for reaction to occur under these conditions, approximately 5 minutes.

4. Compress the ammonia treated biomass, for example in a screw reactor, to minimize the volume of vapor or "dead" space.

5. Further reduce the tendency of ammonia to convert to a gas by, for example, pressurizing the system with an inert gas such as nitrogen, or by mixing finely divided solids such as sand or iron filings with the biomass.

6. Add essentially anhydrous liquid ammonia to the intermediate mixture to obtain a final ammonia level of about 0.5 kg ammonia (as NH$_3$) per kg of dry biomass and temperatures of about 90° C.

7. Hold new mixture at these conditions for an additional 5 minutes.

8. Rapidly release the pressure to remove and recover the ammonia.

9. Hydrolyze the resulting solids to mixtures of simple sugars containing, for example, glucose, xylose and arabinose.

Examples 21 to 36

AFEX Treatment of Corn Stover Under Nitrogen Pressure

The main objective of these series of experiments was twofold:

(1) To establish the fact that the ammonia in the liquid phase where it is in direct contact with the biomass is preferred phase that makes the AFEX an effective pretreatment process. Therefore, to minimize ammonia evaporation, applying nitrogen pressure during pretreatment of biomass is warranted. (2) To optimize the ammonia loading under nitrogen.

Experimental Procedure:

Old corn stover with 36.1% Glucan content was received from NREL (Golden, Colo.). The moisture content of the biomass was adjusted from 10% to the desired level before placing in the reactor. The reactor was a 300 ml PARR unit with pressure and temperature monitoring attachments. The sample in the reactor topped up with some spherical steel balls to reduce the void in the reactor and to have similar conditions with experiments without use of nitrogen.

A predetermined amount of anhydrous ammonia was charged in a reactor using a sample cylinder. Nitrogen gas was introduced to the reactor from a nitrogen cylinder tank via a pressure regulator. The reactor was gradually heated up by a heating mantle until it reached 90° C. After 5 min of residence time, the reactor was depressurized at once. Temperature and pressure were recorded every 2 min during the experiments. The pressure started at about 400 psig and ended at about 750 psig, while the reactor temperature started at about 50° C. and ended at about 90° C. when it was vented.

Experimental Conditions:

Two sets of Experiments were conducted. For the first four Experiments 21 to 24, the previous optimal conditions of 60% dwb biomass moisture content, 90° C. treatment temperature and 5 min residence time was chosen, while the amount of charged ammonia was varied to determine optimal ammonia loading under $N_2$ pressure.

For the second set of 6 Experiments 25 to 30, both the moisture content and ammonia loading was varied. Some of the first set of Experiments was repeated in the second set as well. The repeated Experiments showed similar results. A third set of 6 Experiments 31 to 36, was not conclusive for all the runs possibly due to bad hydrolysis.

Hydrolysis:

For Hydrolysis, NREL Lap-009 protocol was followed. Duplicate samples were prepared and hydrolyzed for a period of 168 hr. At time intervals of 24 hr, 72 hr and 168 hr, samples were taken for HPLC analysis. To all samples were added 15 FPU per g of glucan of Spezyme CP (CAFI 1), Old enzyme with 28.2 FPU/ml.

Analysis:

A Waters High Performance Liquid Chromatography (HPLC) with Aminex HPX 87 P BioRad Column and de-ashing guard column was used to perform the analysis. The analysis was performed in our lab as well as at Michigan Biotechnology International (MBI), East Lansing, Mich.

In the optimized AFEX pretreatment conditions of 1 kg $NH_3$:1 kg DBM, 60% MC, 90° C. ideally, there are 90% glucose and 70% xylose conversions. If the decrease in the amount of ammonia used under nitrogen pressure is back calculated, there is a 1.5, 2 and 5-fold increase in yield under nitrogen pressure proportional to the ammonia loadings of 0.5, 0.3 and 0.1 kg $NH_3$: Kg DBM, respectively. In other words, there is a 5-fold savings on the amount of ammonia when AFEX under nitrogen pressure is employed at 0.1:1 ammonia charge compared to 1:1. The amount of ammonia has decreased 10 times (1:1 to 0.1:10 while both the glucose and xylose yields has dropped to ½ from 90% to 45% and 70% to 35% for glucose and xylose, respectively. The results are shown in FIGS. 3 to 9.

Example 37

Pretreatment of Lignocellulosic Biomass Using Gaseous Ammonia

Anhydrous gaseous ammonia was transferred to a stainless steel cylinder and preheated to reach 450-900 psi. In parallel, the biomass with appropriate moisture (60%) was kept in a preheated (between 140° C. and 160° C. ) stainless steel reaction vessel, a vacuum was applied to remove air and to create negative pressure to facilitate ammonia delivery. The preheated ammonia gas was transferred to the reaction vessel. The un-reacted ammonia in the vessel was measured and the actual ammonia added to the pretreatment reactor during the process was calculated. There was a rapid rise in temperature of the biomass (from 30° C. initial temperature to about 100-200° C.) depending on the pressure/temperature of preheated ammonia gas. The reaction was continued to achieve different residence times and the pressure was then slowly released.

Example 38

Enzymatic Hydrolysis of Corn Stover Pretreated Using AFEX (Control) and GAP Process with Different Ammonia Loading and Residence Times The pretreated biomass was dried in the hood overnight and pretreatment efficiency was determined by digestion of the biomass with commercial enzymes (15 FPU of Spezyme CP from Genencor and 64 pNPGU of beta-glucosidase from Novozyme, per gm glucan) at 50° C. over a period of 72 hrs. The hydrolyzates were analyzed for glucose using YSI glucose analyzer. FIG. 12 shows 5 and 15 minute reaction times using the GAP process, a 45 minute reaction time using the AFEX process, and various ratios of biomass to ammonia. The data in FIG. 12 demonstrates equal or better pretreatment efficiency with GAP using significantly shorter reaction times than AFEX.

Example 39

Biomass Glucan Conversion as a Function of Different GAP Conditions

Figure 13:
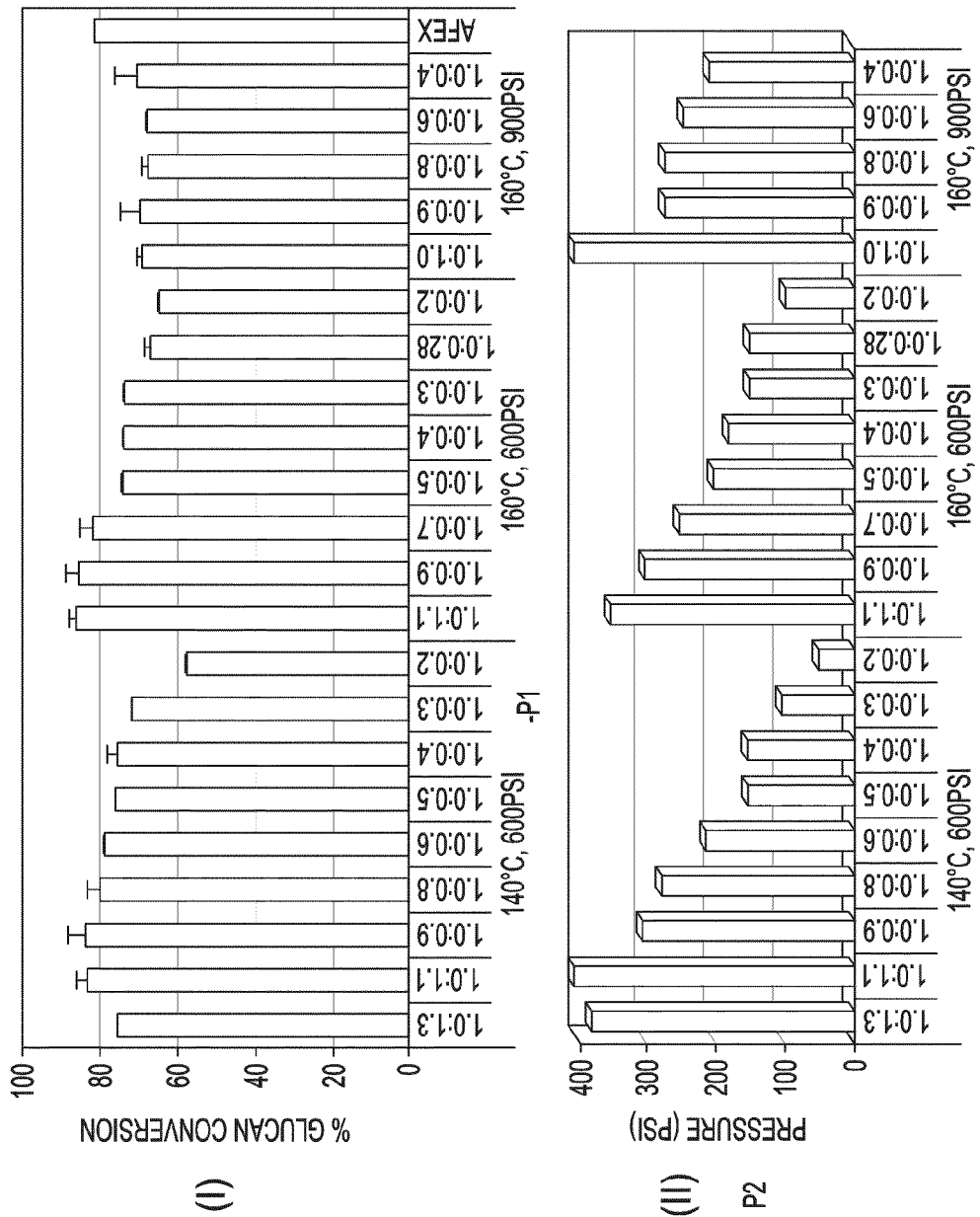
FIG. 13 shows percent glucose yield (% glucan conversion) from treated corn stover as a function of different GAP conditions, the effect of ammonia to biomass loading during the GAP process and the pretreatment effect seen during enzymatic hydrolysis (I) and pressure in the reactor during the process (II). In (I), biomass to ammonia loading is shown on x-axis, which is examined at different pressures P1 and temperatures (of the gaseous ammonia before adding it to the reaction vessel containing corn stover). Also, in (I), the y-axis gives the over glucose yield achieved as a function of various GAP conditions.

In order to further understand the effect of concentration of ammonia needed during GAP process, the biomass moisture was fixed at 60% and the concentration of biomass to ammonia was varied from 1:1.2 to 1:0.2 (biomass to ammonia loading, w/w). In addition, the ammonia delivery pressure P1 (prior to loading) and reactor temperature were varied. These results are shown in FIG. 13. From FIG. 13, it is clear that up to 1:0.8 of the conversions are comparable to conventional AFEX process (60% moisture, 1:1 biomass to ammonia loading, 45 min. total residence time). By further dropping the biomass to ammonia loading (to 1:0.2), there is only a 10-15% drop in glucose yield compared to the control. That is, there is nearly as much percent glucose conversion for GAP treated corn stover as AFEX treated corn stover at significantly lower ammonia loading and pressure in the reaction vessel. In (II), the y-axis in depicts the pressure in the reactor as a function of GAP conditions and shows that the pressure P2 in the reactor decreases with ammonia loading. By reducing the ammonia to biomass loading, the pressure in the reactor vessel also drops (FIG. 13, II) to between 50-150 psi.

Though the glucose yield drops by 10%, the pressure P2 in the reactor vessel also drops below 100 psi. Hence, operational and capital costs for GAP carried out at lower pressure (and low ammonia loadings) will be substantially lower compared to AFEX and other ammonia based pretreatments. With the GAP process, by proper selection of an enzyme cocktail (containing suitable cellulases and hemicellulases), the inventors expect that they can further boost the conversion and reduce processing costs by further lowering biomass to ammonia loading (1:0.05-1:0.2 biomass to ammonia loading, dwb) during the GAP process.

Example 40

Effect of Pressure Release During Pretreatment Process

Figure 14:
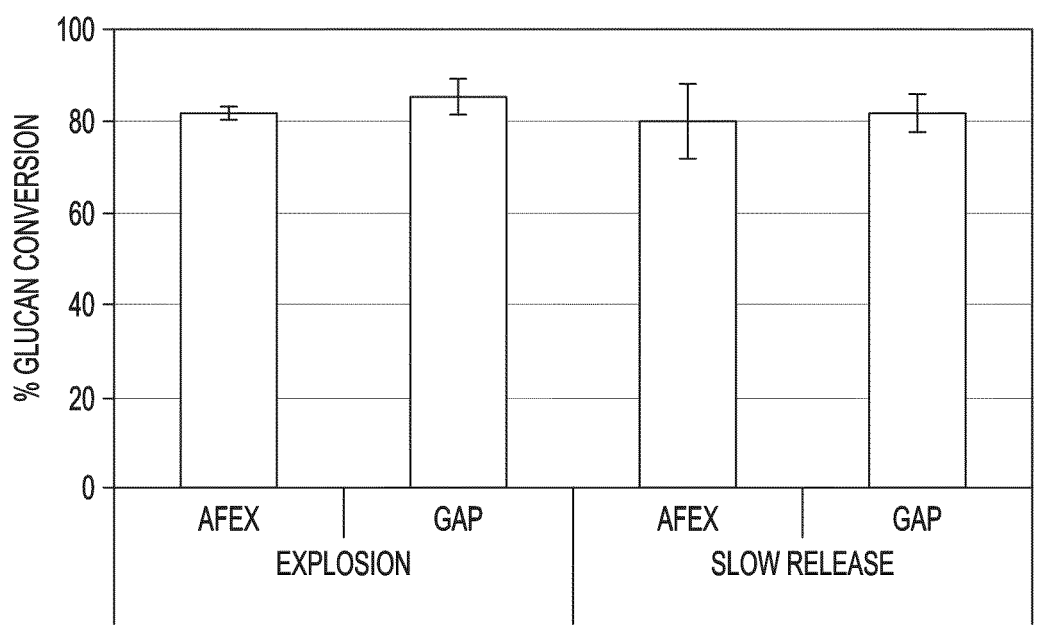
FIG. 14 shows the role of explosive removal of ammonia during AFEX and GAP pretreatment process on glucose yield for treated corn stover.

Two independent pretreatments were peformed using the AFEX and GAP processes, utilizing 1:1 biomass to ammonia loading. In the first set of experiments, the pressure was released explosively. In the second set of experiments, the pressure was released slowly after the process. In explosive release, the pressure was suddenly reduced (under 1 second) from reaction pressure (200-400 psi) to atmospheric pressure (15 psi). In slow release, the pressure was dropped gradually to atmospheric pressure (over 2 minutes to drop pressure). The resultant feed stock was collected in a tray and dried in hood overnight. The next day treated material was tested for digestibility using commercial enzymes at 50° C., for 72 hrs, as described above (FIG. 14). In FIG. 14, the y-axis depicts the % glucose yield (% glucan conversion) for differentially treated biomass samples. The inventors observed marginal decreases in conversion for the pretreatment process performed with slow release as compared to explosion, and this decrease was within the error margin. This indicates that explosive or sudden expansive release of ammonia during pretreatment is unnecessary or not very important. It is therefore possible to continuously pretreat the biomass fed continuously to a constant pressurized reactor fed with hot ammonia gas (and water) and/or inert/carrier gas mixtures.

Example 41

Hydrolysis for Untreated and AFEX-Treated Corn Stover

FIG. 16 shows hydrolysis for untreated and AFEX-treated corn stover. Regular AFEX was performed at 90° C., 1:1 biomass to ammonia loading, at 60% moisture dwb at 5 minutes residence time. Low moisture AFEX was performed at 90° C., 1:1 biomass to ammonia loading at 5% moisture dwb at 5 minutes residence time after 24 hours of incubation at 50° C. at 200 rpm.

In order to prove that low moisture biomass (5% moisture) gives comparable pretreatment results to that of high moisture biomass (60% moisture on dwb), the inventors performed pretreatment for these conditions and enzymatic hydrolysis using 15 FPU of cellulase and 64 pNPGU of beta-glucosidase. The conversion results are shown in FIG. 16. The y-axis depicts the glucose and xylose yields after enzymatic hydrolysis for the various pretreatment conditions.

Figure 17:
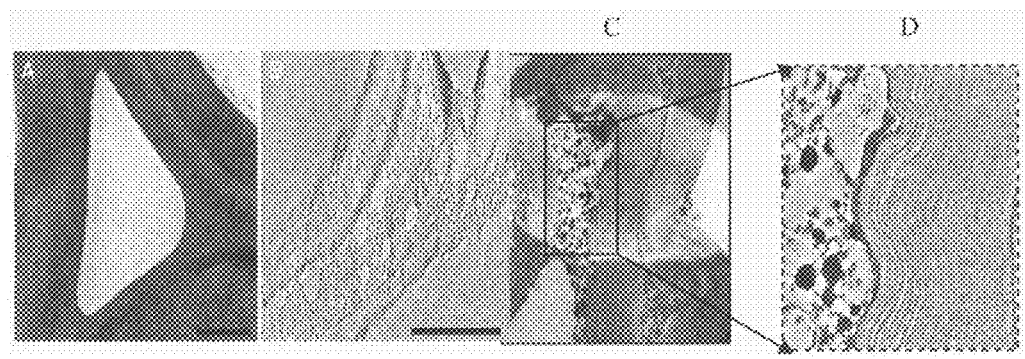
FIGS. 17A-17D show transmission electron micrograph images of untreated and ammonia pretreated corn stover cell walls.

In addition, electron tomographic images have shown that pretreating biomass with low moisture creates more porosity within the cell wall than when using higher moisture content (FIGS. 17A and 17B). The increased porosity would allow better accessibility for the enzymes to hydrolyze pretreated biomass more efficiently. The slightly lower conversion for low moisture AFEX treated sample could be due to lack of suitable hemicellulases during enzymatic hydrolysis and poor heat/mass transfer during AFEX pretreatment.

By proper control of the above-mentioned factors but, instead, using GAP-based fluidization, the inventors expect to obtain better results when compared to regular AFEX conditions. The advantage of low moisture ammonia based treatments, especially during GAP, is the easier recovery of ammonia from water. That is, if there is more the water in the system, it is more expensive it is to recover (and recycle) the ammonia from the system.

Example 42

Comparison of Resource Savings and GHG Emissions

In order to evaluate the energy, resources saving and green house gas emissions (GHG) for the GAP process when compared to the AFEX process, the inventors performed a calculation based on an Aspen plus model and the results are presented in Table 4. The results show substantial amount of heat, electricity and water saving, in addition to a 3-fold reduction in GHG emissions for the GAP process.

TABLE 4

|  | Process Information | | | GHG | | |
| --- | --- | --- | --- | --- | --- | --- |
|  | unit | GAP | APEX | unit: | GAP | APEX |
| Corn stover | m t | 1 | 1 |  |  |  |
| Ammonia | kg | 8.8 | 8.8 | kg | 24 | 25 |
| Water | kg | 0.0 | 896 | kg | 0 | 1 |
| Electricity | MJ | 19 | 33 | kg | 4 | 7 |
| Heat | MJ | 449 | 2521 | kg | 35 | 194 |
| biomass* | m t | 1.0 | 1.0 |  |  |  |
| Total |  |  |  |  | 63 | 226 |

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention.

REFERENCES

1. Walter A. (2000), in Industrial uses of biomass energy, edited by Rosillo-Calle F., Bajay S V, Rothman H, pp 200-253, Taylor & Francis.
2. Eggeman T, Elander R T (2005) Process and economic analysis of pretreatment technologies. Bioresour Technol 96:2019-2025.

3. Somerville C, Bauer S, Brininstool G, Facette M, Hamann T, Milne J, Osborne E, Paredez A, Persson S, Raab T, Vorwerk S, Youngs H. (2004) Toward a Systems Approach to Understanding Plant Cell Walls. Science 306:2206-2211.
4. Cosgrove D J (2005) Growth of the plant cell wall. Nature review 6:850-861.
5. Mosier N, Wyman C, Dale B, Elander R, Lee Y Y, Holtzapple M, Ladisch M (2005) Features of promising technologies for pretreatment of lignocellulosic biomass. Bioresour Technol 96(6):673-686.
6. Dale B E (1986) Method for increasing the reactivity and digestibility of cellulose with ammonia. U.S. Pat. No. 4,600,590.
7. Dale B E (1991) Process for increasing the reactivity of cellulose containing material. U.S. Pat. No. 5,037,663.
8. Dale B E (2000) Process for treating cellulosic materials. U.S. Pat. No. 6,106,888.
9. Dale B E and Weaver J K (2001) Apparatus for treating cellulosic materials. U.S. Pat. No. 6,176,176 B1.
10. Teymouri F, Laureano-Perez L, Alizadeh H, Dale B E (2005) Optimization of the ammonia fiber explosion (AFEX) treatment parameters for enzymatic hydrolysis of corn stover. Bioresource Technol 96:2014-2018.
11. Chundawat P S, Venkatesh B, Dale B E (2007) Effect of Particle Size Based Separation of Milled Corn Stover on AFEX pretreatment and Enzymatic Digestibility. Biotechnol Bioeng 96:219-231.
12. Chou, Y-CT (1987) Supercritical ammonia treatment of lignocellulosic materials. U.S. Pat. No. 4,644,060.
13. Hennessey S M, Friend J, Dunson J B, Tucker M P, Elander R T and Hames B. (2007) Integration of alternative feedstreams for biomass treatment and utilization. Patent No. US 2007/0037259 A1.
14. Dunson J R, Tucker M P, Elander R T and Lyons R C (2007) System and Process for Biomass treatment. Patent No. US2007/0029252 A1.
15. Kim T H, Lee Y Y, Sunwoo C, Kim J S. (2006) Pretreatment of corn stover by low-liquid ammonia recycle percolation process. Appl. Biochem. Biotechnol. 133:41-57.
16. Erickson D R (1990) Edible fats and oil processing-Basic principle and modern practices. AOCS Press, Netherlands.
17. Pivai G, Galvanoz F, Pietril A, Piva A (1995) Detoxification Methods of Flatoxins-A Review. Nutrition Research, 15(5):767-776.
18. Prevot-D'Alvise N, Lesueur-Lambert C, Fertin-Bazus A, Fertin B and Dhulster P (2003) Development of a pilot process for the production of alfalfa peptide isolate. J. Chem. Technol. Biotechnol. 78:518-528.

What is claimed is:

1. A method for treating biomass comprising:
    adding gaseous ammonia at an elevated temperature to a reaction vessel containing biomass, wherein the reaction vessel is operated under a pressure of about 100 psi to about 1000 psi;
    allowing the gaseous ammonia to condense on the biomass and react with water present in the biomass, to produce a pretreated biomass, wherein the reaction vessel pressure is released over a period of greater than two minutes; and
    removing residual ammonia present in the reaction vessel.
2. The method of claim 1 wherein the biomass has a temperature which increases substantially instantaneously due to an exothermic reaction between the water and gaseous ammonia react.
3. The method of claim 2 wherein the biomass temperature is between about 50° C. and about 200° C.
4. The method of claim 1 wherein the gaseous ammonia is delivered to the reaction vessel under pressure.
5. The method of claim 1 wherein the biomass is comprised of about 5% to about 233% water on a dry weight basis.
6. The method of claim 1 wherein the biomass is comprised of about 5% to about 60% water on a dry weight basis.
7. The method of claim 1 wherein the gaseous ammonia reacts with the water in the biomass for about 1 minute to about 120 minutes.
8. The method of claim 7 wherein the gaseous ammonia reacts with the water in the biomass for about 1 minute to about 20 minutes.
9. The method of claim 1 wherein the method is a continuous method or a semi-batch method.
10. The method of claim 1 further comprising delivering a carrier to the reaction vessel.
11. The method of claim 10 wherein the carrier is combined with the gaseous ammonia.
12. The method of claim 10 wherein the carrier is steam.
13. The method of claim 10 wherein the carrier is an oxidative carrier or an inert gas.
14. The method of claim 13 wherein the oxidative carrier is air and the inert gas is nitrogen.
15. The method of claim 1 wherein the reaction vessel is selected from a fluidized bed reactor, a fixed bed reactor and a semi-fluidized bed reactor.
16. The method of claim 1 wherein at least a portion of the water present in the biomass is added water.
17. The method of claim 1 wherein a biomass to ammonia ratio is from about 1:0.2 to about 1:2.
18. The method of claim 1 wherein the residual ammonia present in reaction vessel is removed with steam.
19. The method of claim 18 wherein the biomass to ammonia ratio is from about 1:0.2 to about 1:1.
20. The method of claim 1 wherein a biomass to ammonia ratio is from about 1:0.01 to about 1:5.
21. The method of claim 1 wherein the reaction vessel pressure is from about 200 psi to about 500 psi.
22. The method of claim 1 wherein the reaction vessel pressure is released over a period of greater than two minutes prior to the removing step.
23. The method of claim 22 further comprising recovering the gaseous ammonia provided to the reaction vessel and recycling at least a portion of said gaseous ammonia and at least a portion of the residual ammonia.
24. The method of claim 23 wherein at least 50% of said gaseous ammonia is recovered and recycled.
25. The method of-claim 23 wherein from about 50% to about 99.5% of said gaseous ammonia is recovered and recycled.
26. The method of claim 23 wherein the biomass is treated with a mixture of recycled gaseous ammonia and steam.
27. The method of claim 1 wherein the biomass has a moisture content of less than about 15% dry weight basis.
28. The method of claim 1 further comprising impregnating the biomass with ammonia prior to the allowing step.
29. The method of claim 28 wherein a biomass to ammonia ratio is from about 1:0.01 to about 1:0.3.
30. The method of claim 28 wherein the biomass is fed to the reaction vessel continuously.

* * * * *

UNITED STATES PATENT AND TRADEMARK OFFICE
CERTIFICATE OF CORRECTION

PATENT NO. : 8,968,515 B2
APPLICATION NO. : 12/976344
DATED : March 3, 2015
INVENTOR(S) : Venkatesh Balan et al.

It is certified that error appears in the above-identified patent and that said Letters Patent is hereby corrected as shown below:

Title Page

Page 3/Other Publications/Col. 1/Line 54: Error reads as "Anaylsis" and should read as "Analysis"
Page 3/Other Publications/Col. 2/Line 28: Error reads as "Intergrated" and should read as "Integrated"
Page 4/Other Publications/Col. 1/Line 63: Error reads as "Faciliyt" and should read as "Facility"
Page 4/Other Publications/Col. 2/Line 32: Error reads as "Biochecmical" and should read as "Biochemical"
Page 4/Other Publications/Col. 2/Line 44: Error reads as "Onbiotechnology" and should read as "on Biotechnology"
Page 7/Other Publications/Col. 1/Line 13: Error reads as "Amrnonia" and should read as "Ammonia"
Page 7/Other Publications/Col. 1/Line 60: Error reads as "Fungl," and should read as "Fungi,"
Page 7/Other Publications/Col. 1/Line 62: Error reads as "Deveopment" and should read as "Development"
Page 7/Other Publications/Col. 2/Line 44: Error reads as "Cellutase" and should read as "Cellulase"
Page 7/Other Publications/Col. 2/Line 52: Error reads as "Bioresouce" and should read as "Bioresource"
Page 7/Other Publications/Col. 2/Line 71: Error reads as "logen's" and should read as "logan's"
Page 8/Other Publications/Col. 1/Line 16: Error reads as "Hurnana" and should read as "Humana"
Page 8/Other Publications/Col. 2/Line 70: Error reads as "Commercialiy" and should read as "Commercially"
Page 9/Other Publications/Col. 1/Line 37: Error reads as "Biotechnolology," and should read as "Biotechnology,"
Page 9/Other Publications/Col. 2/Line 1: Error reads as "AFEX-trealed" and should read as "AFEX-treated"

In the Specification

Col. 1/Lines 63-64: Error reads as "concentrated ammonia (AFEX™)" and should read as "concentrated ammonia, (AFEX™)"

Signed and Sealed this
Twenty-eighth Day of July, 2015

Michelle K. Lee
*Director of the United States Patent and Trademark Office*

CERTIFICATE OF CORRECTION (continued)
U.S. Pat. No. 8,968,515 B2

Col. 8/Line 46: Error reads as "distinctinctive" and should read as "distinctive"
Col. 21/Line 29: Error reads as "peformed" and should read as "performed"
Col. 23/Line 44: Error reads as "Flatoxins-A" and should read as "Aflatoxins-A"

In the Claims

Col. 23/Line 64/Claim 2: Error reads as "gaseous" and should read as "the gaseous"
Col. 24/Line 6/Claim 6: Error reads as "of" and should read as "of from"
Col. 24/Line 52/Claim 25: Error reads as "of-claim" and should read as "of claim"